United States Patent
Caroff et al.

(10) Patent No.: US 10,053,457 B2
(45) Date of Patent: Aug. 21, 2018

(54) HYDROXYALKYL-PIPERAZINE DERIVATIVES AS CXCR3 RECEPTOR MODULATORS

(71) Applicant: IDORSIA PHARMACEUTICALS LTD, Allschwil (CH)

(72) Inventors: Eva Caroff, Allschwil (CH); Emmanuel Meyer, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 15/543,457

(22) PCT Filed: Jan. 14, 2016

(86) PCT No.: PCT/EP2016/050645
§ 371 (c)(1),
(2) Date: Jul. 13, 2017

(87) PCT Pub. No.: WO2016/113344
PCT Pub. Date: Jul. 21, 2016

(65) Prior Publication Data
US 2018/0009799 A1   Jan. 11, 2018

(30) Foreign Application Priority Data
Jan. 15, 2015  (WO) ............... PCT/EP2015/050696

(51) Int. Cl.
*A61K 31/506*    (2006.01)
*C07D 417/14*    (2006.01)

(52) U.S. Cl.
CPC ................. *C07D 417/14* (2013.01)

(58) Field of Classification Search
CPC .................................................. C07D 417/14
See application file for complete search history.

(56) References Cited

U.S. PATENT DOCUMENTS

| | | | |
|---|---|---|---|
| 7,589,199 B2 | 9/2009 | Pennell et al. | |
| 7,645,755 B2 | 1/2010 | Illig et al. | |
| 7,842,693 B2 | 11/2010 | Pennell et al. | |
| 8,324,216 B2 | 12/2012 | Pennell et al. | |
| 8,450,317 B2 | 5/2013 | Kowalski et al. | |
| 8,889,677 B2 | 11/2014 | Grauert et al. | |
| 9,266,876 B2 * | 2/2016 | Caroff | C07D 417/14 |
| 9,732,075 B2 * | 8/2017 | Boss | C07D 401/14 |
| 9,850,256 B2 * | 12/2017 | Cren | C07D 498/04 |
| 2004/0082571 A1 | 4/2004 | Pennell et al. | |
| 2005/0256130 A1 | 11/2005 | Pennell et al. | |
| 2006/0276465 A1 | 12/2006 | Kawahara et al. | |
| 2008/0139572 A1 | 6/2008 | Wang et al. | |
| 2010/0094006 A1 | 4/2010 | Nam et al. | |
| 2011/0136823 A1 | 6/2011 | Deprez et al. | |
| 2013/0072497 A1 | 3/2013 | Lorsbach et al. | |
| 2014/0371204 A1 * | 12/2014 | Caroff | C07D 417/14 |
| | | | 514/210.21 |
| 2016/0176862 A1 * | 6/2016 | Caroff | C07D 417/14 |
| | | | 514/252.19 |
| 2017/0107214 A1 * | 4/2017 | Caroff | C07D 401/14 |
| 2017/0305897 A1 * | 10/2017 | Boss | C07D 417/14 |
| 2018/0009799 A1 * | 1/2018 | Caroff | C07D 417/14 |
| 2018/0009800 A1 * | 1/2018 | Caroff | C07D 417/14 |

FOREIGN PATENT DOCUMENTS

| | | |
|---|---|---|
| EP | 1698620 A1 | 9/2006 |
| WO | WO 2002/059107 A1 | 8/2002 |
| WO | WO 2002/059108 A1 | 8/2002 |
| WO | WO 2002/070511 A1 | 9/2002 |
| WO | WO 2005/003127 A1 | 1/2005 |
| WO | WO 2005/035534 A1 | 4/2005 |
| WO | WO 2005/040136 A1 | 5/2005 |
| WO | WO 2005/042516 A2 | 5/2005 |
| WO | WO 2005/044797 A1 | 5/2005 |

(Continued)

OTHER PUBLICATIONS

Wang et al., 19 Bioorganic and Medicinal Chemistry Letters, 114-118 (2009).*
I.L. Stroke et al., 349 Biochemical and Biophysical Research Communications, 221-228 (2006).*
C. Billottet et al., 1836 Biochimica et Biophysica Acta, 287-295 (2013).*
A. Fulton, 11 Current Oncology Reports, 125-131 (2009).*
D. Jiang et al., 114 The Journal of Clinical Investigation, 299-291 (2004).*
Y. Ha et al., 6 Cell Death and Disease, 1-11 (2015) (neurodegeneration).*
M. Krauthausen et al., 125 The Journal of Clinical Investigation, 365-378 (2015).*
A. Denoyer et al., 7 PLoS One, 1-11 (2012).*
S.V. Campanella et al., 105 PNAS, 4814-4819 (2012).*

(Continued)

*Primary Examiner* — Alexander R Pagano
(74) *Attorney, Agent, or Firm* — Arent Fox LLP

(57) ABSTRACT

The invention relates to compounds of Formula (I)

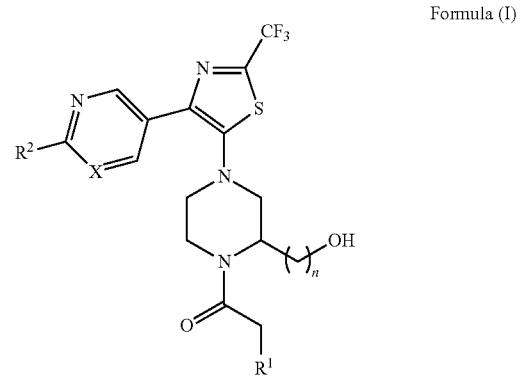

Formula (I)

wherein n, X, $R^1$ and $R^2$ are as described in the description; to pharmaceutically acceptable salts thereof, and to the use of such compounds as medicaments, especially as modulators of the CXCR3 receptor.

21 Claims, No Drawings

(56) References Cited

FOREIGN PATENT DOCUMENTS

| | | |
|---|---|---|
| WO | WO 2005/051304 A2 | 6/2005 |
| WO | WO 2006/047277 A2 | 5/2006 |
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2007/002293 A2 | 1/2007 |
| WO | WO 2007/002742 A1 | 1/2007 |
| WO | WO 2007/014290 A2 | 2/2007 |
| WO | WO 2007/047202 A1 | 4/2007 |
| WO | WO 2007/048088 A2 | 4/2007 |
| WO | WO 2007/064533 A2 | 6/2007 |
| WO | WO 2007/070433 A2 | 6/2007 |
| WO | WO 2007064553 A2 | 6/2007 |
| WO | WO 2007070433 A2 | 6/2007 |
| WO | WO 2007/076318 A2 | 7/2007 |
| WO | WO 2007/100610 A2 | 9/2007 |
| WO | WO 2007/109238 A1 | 9/2007 |
| WO | WO 2007/124369 A2 | 11/2007 |
| WO | WO 2007/127635 A2 | 11/2007 |
| WO | WO 2008/003861 A1 | 1/2008 |
| WO | WO 2008/008453 A1 | 1/2008 |
| WO | WO 2008/013622 A2 | 1/2008 |
| WO | WO 2008/013925 A2 | 1/2008 |
| WO | WO 2008/079279 A1 | 7/2008 |
| WO | WO 2008/091580 A2 | 7/2008 |
| WO | WO 2008/091594 A2 | 7/2008 |
| WO | WO 2008/147822 A1 | 12/2008 |
| WO | WO 2009/020534 A2 | 2/2009 |
| WO | WO 2009/055514 A2 | 4/2009 |
| WO | WO 2009/079490 A1 | 6/2009 |
| WO | WO 2009/094407 A2 | 7/2009 |
| WO | WO 2009/094445 A2 | 7/2009 |
| WO | WO 2009/105435 A1 | 8/2009 |
| WO | WO 2009/132785 A1 | 11/2009 |
| WO | WO 2010/037479 A1 | 4/2010 |
| WO | WO 2010/065579 A2 | 6/2010 |
| WO | WO 2010/066353 A1 | 6/2010 |
| WO | WO 2010/126811 A1 | 11/2010 |
| WO | WO 2010/126851 A1 | 11/2010 |
| WO | WO 2010/149275 A1 | 12/2010 |
| WO | WO 2011/018401 A1 | 2/2011 |
| WO | WO 2011/018415 A2 | 2/2011 |
| WO | WO 2011/051243 A1 | 5/2011 |
| WO | WO 2011/051244 A1 | 5/2011 |
| WO | WO 2011/076699 A1 | 6/2011 |
| WO | WO 2011/084985 A1 | 7/2011 |
| WO | WO 2011/134969 A1 | 11/2011 |
| WO | WO 2011/144586 A1 | 11/2011 |
| WO | WO 2011/146182 A1 | 11/2011 |
| WO | WO 2011/147765 A1 | 12/2011 |
| WO | WO 2012/020060 A1 | 2/2012 |
| WO | WO 2012/025557 A1 | 3/2012 |
| WO | WO 2012/055837 A1 | 5/2012 |
| WO | WO 2012/069633 A1 | 5/2012 |
| WO | WO 2012/082580 A2 | 6/2012 |
| WO | WO 2012/104273 A1 | 8/2012 |
| WO | WO 2012/107475 A1 | 8/2012 |
| WO | WO 2012/107477 A1 | 8/2012 |
| WO | WO 2012/171337 A1 | 12/2012 |
| WO | WO 2013/037768 A1 | 3/2013 |
| WO | WO 2013/056911 A1 | 4/2013 |
| WO | WO 2013/056915 A1 | 4/2013 |
| WO | WO 2013/083741 A1 | 6/2013 |
| WO | WO 2013/107761 A1 | 7/2013 |
| WO | WO 2013/110134 A1 | 8/2013 |
| WO | WO 2013/114332 A1 | 8/2013 |
| WO | WO 2013114332 A1 | 8/2013 |
| WO | WO 2013/127784 A1 | 9/2013 |
| WO | WO 2013/127808 A1 | 9/2013 |
| WO | WO 2014/062938 A1 | 4/2014 |
| WO | WO 2014/075873 A1 | 5/2014 |
| WO | WO 2014/075874 A1 | 5/2014 |
| WO | WO 2014/092100 A1 | 6/2014 |
| WO | WO 2014/206896 A1 | 12/2014 |
| WO | WO 2015/011099 A1 | 1/2015 |
| WO | WO 2015/026683 A1 | 2/2015 |
| WO | WO 2015/145322 A1 | 10/2015 |
| WO | WO 2016/113346 A1 | 7/2016 |

OTHER PUBLICATIONS

U.S. Office Action issued in U.S. Appl. No. 15/128,846 dated Sep. 14, 2017.
Greene, Theodora W. et al., "Protective Groups in Organic Synthesis" Third Edition, Wiley-Interscience, 1999.
Groom, Joanna R. et al., "CXCR3 in T cell function" Experimental Cell Research 317, 2011, pp. 620-631.
Groom, Joanna R. et al., "CXCR3 ligands: redundant, collaborative and antagonistic functions" Immunology and Cell Biology, 2011.
Hancock, Wayne W., "Requirement of the Chemokine Receptor CXCR3 for Acute Allograft Rejection" J. Exp. Med., vol. 192, No. 10, pp. 1515-1519, Nov. 20, 2000.
Jenh, Chung-Her et al., "A selective and potent CXCR3 antagonist SCH 546738 attenuates the development of autoimmune diseases and delays graft rejection" BMC Immunology, vol. 13, No. 2, 2012.
Lacotte, Stephanie et al., "CXCR3, Inflammation, and Autoimmune Diseases" Annals of the New York Academy of Sciences 1173, pp. 310-317, 2009.
Lammers, Karen M. et al., "Gliadin Induces an Increase in Intestinal Permeability and Zonulin Release by Binding to the Chemokine Receptor CXCR3" Gastroenterology, vol. 135, No. 1, pp. 194-204, 2008.
Mach, Francois et al., "Differential expression of three T lymphocyte-activating CXC chemokines by human atheroma-associated cells" The Journal of Clinical Investigation, vol. 104, No. 8, pp. 1041-1050, Oct. 1999.
McGuinness, Brian F. et al., "Novel CXCR3 Antagonists with a Piperazinyl-Piperidine Core" Bioorganic & Medicinal Chemistry Letters, 2009.
Menke, Julia et al., "Distinct Roles of CSF-1 Isoforms in Lupus Nephritis" Journal of the American Society of Nephrology 22, pp. 1821-1833, 2011.
Mohan, Karkada et al.,"Blockade of Chemokine Receptor CXCR3 Inhibits T Cell Recruitment to Inflamed Joints and Decreases the Severity of Adjuvant Arthritis" The Journal of Immunology, 179, pp. 8463-8469, 2007.
Nie, Li et al., "Attenuation of acute lung inflammation induced by cigarette smoke in CXCR3 knockout mice" Respiratory Research, vol. 9, No. 82, 2008.
Pradelli, Emmanuelle et al., "Antagonism of chemokine receptor CXCR3 inhibits osteosarcoma metastasis to lungs" Int J. Cancer, vol. 125, pp. 2586-2594, 2009.
Prokopowicz, A. et al., "Optimization of a biaryl series of CXCR3 antagonists" ACS National Meeting, Philadelphia, US, August.
Reinhart, Peter H., "Identification of anti-inflammatory targets for Huntington's disease using a brain slice-based screening assay" Neurobiology of Disease 43, pp. 248-256, 2011.
Remington, "The Science and Practice of Pharmacy, 21st Edition" Part 5, 2005, Pharmaceutical Manufacturing, Lippincott Williams & Wilkins.
Saetta, Marina et al., "Increased Expression of the Chemokine Receptor CXCR3 and its Ligand CXCL10 in Peripheral Airways of Smokers with Chronic Obstructive Pulmonary Disease" American Journal of Respiratory and Critical Care Medicine, vol. 165, pp. 1404-1409, 2002.
Sakthivel, Senthilkumar K. et al.,"CXCL10 blockade protects mice from cyclophosphamide-induced cystitis" Journal of Immune Based Therapies and Vaccines 2008, 6:6.
Singh, Udai P., "CXCL10-Producing Mucosal CD4+ T Cells, NK Cells, and NKT Cells are Associated with Chronic Colitis in IL-10-/-Mice, Which Can be Abrogated by Anti-CXCL10 Antibody Inhibition" J Interferon Cytokine Res. 28(1), pp. 31-43, Jan. 2008.

(56) References Cited

OTHER PUBLICATIONS

Stahl, Heinrich P et al., "Handbook of Pharmaceutical Salts Properties, Selection, and Use" International Union of Pure and Applied Chemistry (IUPAC), Wiley-VCH, 2008.

Tacke, Frank et al., "Serum chemokine receptor CXCR3 ligands are associated with progression, organ dysfunction and complications of chronic liver diseases" Liver International, vol. 31, pp. 840-849, 2011.

Trentin, Livio et al., "The chemokine receptor CXCR3 is expressed on malignant B cells and mediates chemotaxis" The Journal of Clinical Investigation, vol. 104, No. 1, pp. 115-121, Jul. 1999.

Van Weering, Hilmar R.J. et al., "CXCL10/CXCR3 Signaling in Glia Cells Differentially Affects NMDA-Induced Cell Death in CA and DG Neurons of the Mouse Hippocampus" Hippocampus, 2010.

Veillard, Niels R., "Differential Influence of Chemokine Receptors CCR2 and CXCR3 in Development of Atherosclerosis in Vivo" Circulation, vol. 112, pp. 870-878, 2005.

Wang, Yonghui et al., "Camphor sulfonamide derivatives as novel, potent and selective CXCR3 antagonists" Bioorganic & Medicinal Chemistry Letters 19, pp. 114-118, 2009.

Watson, Robert J. et al., "Development of CXCR3 antagonists. Part 2: Indentification of 2-amino(4-piperidinyl)azoles as potent CXCR3 antagonists" Bioorganic & Medicinal Chemistry Letters 17, pp. 6806-6810, 2007.

Wijtmans, Maikel et al., "Towards Small-Molecule CXCR3 Ligands with Clinical Potential" vol. 3, pp. 861-872, 2008.

Wouters, Johan et al., "Pharmaceutical Salts and Co-crystals" RSC Publishing, RSC Drug Discovery Series No. 16, 2012.

Zhang, Feiran et al., "Pyridinylquinazolines Selectively Inhibit Human Methionine Aminopeptidase-1 in Cells" Journal of Medicinal Chemistry, vol. 56, pp. 3996-4016, 2013.

International Search Report issued in International Application No. PCT/EP2016/050645 dated Jun. 29, 2017.

* cited by examiner

HYDROXYALKYL-PIPERAZINE DERIVATIVES AS CXCR3 RECEPTOR MODULATORS

CROSS-REFERENCE TO RELATED APPLICATION

This application is a 35 U.S.C. § 371 National Phase of PCT Application No. PCT/EP2016/050645 filed Jan. 14, 2016 which claims priority to PCT Application No. PCT/EP2015/050696 filed Jan. 15, 2015. The disclosure of these prior applications are hereby incorporated by reference herein.

The present invention relates to novel hydroxyalkyl-piperazine derivatives of Formula (I), and their use as pharmaceuticals. The invention also concerns related aspects including processes for the preparation of the compounds, pharmaceutical compositions containing one or more compounds of Formula (I), and especially their use as CXCR3 receptor modulators.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

The chemokine receptor CXCR3 is a G-protein coupled receptor binding to the inflammatory chemokines CXCL9 (initially called MIG, monokine induced by interferon-γ [INF-γ]), CXCL10 (IP-10, INF-γ-inducible protein 10), and CXCL11 (I-TAC, INF-γ-inducible T cell α chemo-attractant). CXCR3 is mainly expressed on activated T helper type 1 (Th1) lymphocytes, but is also present on natural killer cells, macrophages, dendritic cells and a subset of B lymphocytes. The three CXCR3 ligands are expressed mainly under inflammatory conditions, expression in healthy tissue is very low. Cells that can express CXCR3 ligands, for instance after exposure to inflammatory cytokines such as interferon-γ or TNF-α, include diverse stromal cells such as endothelial cells, fibroblasts, epithelial cells, keratinocytes but also includes hematopoietic cells such as macrophages and monocytes. The interaction of CXCR3 and its ligands (henceforth referred to as the CXCR3 axis) is involved in guiding receptor bearing cells to specific locations in the body, particularly to sites of inflammation, immune injury and immune dysfunction and is also associated with tissue damage, the induction of apoptosis, cell growth, and angiostasis. CXCR3 and its ligands are upregulated and highly expressed in diverse pathological situations including autoimmune disorders, inflammation, infection, transplant rejection, fibrosis, neurodegeneration and cancer.

A role of the CXCR3 axis in autoimmune disorders is corroborated by several preclinical and clinical observations. Autoimmune disorders in which histological analysis of inflammatory lesions or serum levels of patients revealed elevated levels of CXCR3 ligands or increased numbers of CXCR3 positive cells include rheumatoid arthritis (RA), systemic lupus erythematosus (SLE), lupus nephritis, multiple sclerosis (MS), inflammatory bowel disease (IBD; comprising Crohn's disease and ulcerative colitis), and type I diabetes mellitus (Groom, J. R. & Luster, A. D. Immunol Cell Biol 2011, 89, 207; Groom, J. R. & Luster, A. D. Exp Cell Res 2011, 317, 620; Lacotte, S., Brun, S., Muller, S. & Dumortier, H. Ann N Y Acad Sci 2009, 1173, 310). As expression of CXCR3 ligands is very low in healthy tissue, the above cited correlative evidence strongly suggest a role for CXCR3 in human autoimmune diseases.

Preclinical disease models performed with CXCR3 deficient mice, mice deficient for one of the CXCR3 ligands or the use of antibodies blocking the function of either CXCR3 or one of its ligands further corroborate a role for the CXCR3 axis in immune pathology. For instance, it has been shown that mice deficient for either CXCR3 or the CXCR3 ligand CXCL9 show reduced pathology in a model for lupus nephritis (Menke, J. et al. J Am Soc Nephrol 2008, 19, 1177). In an animal model for another form of kidney inflammation, interstitial cystitis, administration of an antibody blocking CXCL10 function was shown to reduce pathology in cyclophosphamide-induced cystitis (Sakthivel, S. K. et al. J Immune Based Ther Vaccines 2008, 6, 6). Similarly, blocking CXCL10 with an antibody reduced pathology in a rat model of rheumatoid arthritis (Mohan, K. & Issekutz, T. B. J Immunol 2007, 179, 8463). Similarly, in a murine model of inflammatory bowel disease, a blocking antibody against CXCL10 could prevent pathology in a therapeutic setting (Singh, U. P. et al. J Interferon Cytokine Res 2008, 28, 31). Further, experiments performed with tissue from CXCR3 deficient mice suggests a role for CXCR3 in celiac disease, another autoimmune type disorder (Lammers, K. M. et al. Gastroenterology 2008, 135, 194).

Inflammatory diseases that are associated with an elevated expression of the CXCR3 axis include chronic obstructive pulmonary disorder (COPD), asthma, sarcoidosis, atherosclerosis and myocarditis (Groom, J. R. & Luster, A. D. Immunol Cell Biol 2011, 89, 207; Groom, J. R. & Luster, A. D. Exp Cell Res 2011, 317, 620).

One study has shown that CXCR3 positive cells are increased in the lungs of smokers with COPD compared to healthy subjects and immunoreactivity for the CXCR3-ligand CXCL10 was present in the bronchiolar epithelium of smokers with COPD but not in the bronchiolar epithelium of smoking and nonsmoking control subjects (Saetta, M. et al. Am J Respir Crit Care Med 2002, 165, 1404). These findings suggest that the CXCR3 axis may be involved in the immune cell recruitment that occurs in peripheral airways of smokers with COPD. In agreement with these observations, a preclinical study of COPD revealed an attenuation of acute lung inflammation induced by cigarette smoke in CXCR3 deficient mice (Nie, L. et al. Respir Res 2008, 9, 82).

In one investigation of atherosclerosis, CXCR3 expression was found on all T cells within human atherosclerotic lesions. CXCR3 ligands CXCL9, CXCL10 and CXCL11 were all found in endothelial and smooth muscle cells associated with those lesions, suggesting that they are involved in the recruitment and retention of CXCR3 positive cells, particularly activated T lymphocytes, observed within vascular wall lesions during atherogenesis (Mach, F. et al. J Clin Invest 1999, 104, 1041).

Preclinical studies further support a role of CXCR3 in the development of atherosclerosis. CXCR3 genetic deletion in mice lacking ApoE results in a significantly reduced atherosclerotic lesion development within abdominal aortas (Veillard, N. R. et al. Circulation 2005, 112, 870).

A pivotal role for the CXCR3 axis has also been suggested in rejection reactions after organ transplantation and bone marrow transplantation related toxicity (Groom, J. R. & Luster, A. D. Exp Cell Res 2011, 317, 620). Preclinically, CXCR3 deficient mice show a significant resistance to allograft rejection (Hancock, W. W. et al. J Exp Med 2000, 192, 1515).

CXCR3 ligand plasma concentrations also positively correlate with diverse liver pathologies, including liver cirrhosis and fibrosis in humans (Tacke, F., et al. Liver Int 2011, 31, 840).

In the field of oncology, blocking the CXCR3 axis has been proposed to help limit the metastatic spread of cancer cells. For instance, administration of the small molecule CXCR3 receptor antagonist AMG487 could limit the metastasis of tumor cells to the lungs (Pradelli, E. et al. Int J Cancer 2009, 125, 2586). Functional evidence for a role of CXCR3 in regulating B-cell chronic lymphocytic leukemia (CLL) was reported by Trentin and coworkers (Trentin, L. et al. J Clin Invest 1999, 104, 115).

In the central nervous system, blocking the CXCR3 axis may have beneficial effects and prevent neurodegeneration. Increased expression of CXCL10 in the CNS has been demonstrated in ischemia, Alzheimer's disease, multiple sclerosis (MS), and human immunodeficiency virus (HIV)-encephalitis. For example, ex vivo experiments have shown that tissue derived from either CXCR3 or CXCL10 deficient mice, neuronal cell death was diminished after neurotoxic NMDA-treatment when compared to tissue derived from wild type mice (van Weering, H. R. et al. Hippocampus 2011, 21, 220). In a study looking to indentify drug-like molecules that provide neuroprotection against HTT fragment-induced neurodegeneration in a model for Huntington's disease, two CXCR3 receptor antagonists were identified (Reinhart, P. H. et al. Neurobiol Dis 2011, 43, 248.)

4-Thiazolyl-piperidine derivatives as CXCR3 receptor modulators have been disclosed in WO 2007/064553 and WO 2007/070433.

Different 1-(Piperazin-1-yl)-2-heteroaryl-ethanone derivatives as CXCR3 receptor modulators have been disclosed in WO 2007/100610, WO 2010/126811, WO 2013/114332, WO 2015/011099, WO 2015/145322 and on a poster presentation (A. Prokopowicz et al., *Optimization of a biaryl series of CXCR3 antagonists*, 244th ACS National Meeting, Philadelphia, US, Aug. 19-23, 2012).

It has now been found that hydroxyalkyl-piperazine derivatives of Formula (I) are potent CXCR3 modulators which may be useful for the treatment of diseases that are mediated or sustained through the CXCR3 axis, including autoimmune disorders (e.g. rheumatoid arthritis, multiple sclerosis, inflammatory bowel disease, systemic lupus erythematosus, lupus nephritis, interstitial cystitis, celiac disease), inflammatory disorders (e.g. asthma, COPD, atherosclerosis, myocarditis, sarcoidosis), transplantation rejection, fibrosis (e.g. liver cirrhosis), neurodegeneration and conditions involving neuronal death (e.g. Alzheimer's disease, Huntington's disease), and cancer.

1) In a first embodiment, the present invention relates to compounds of Formula (I)

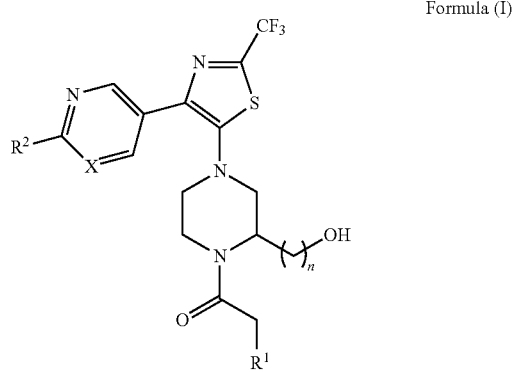

Formula (I)

wherein
n represents the integer 1 or 2;
X represents N or CH;
$R^1$ represents heteroaryl, wherein the heteroaryl is a 5- to 10-membered monocyclic or bicyclic aromatic ring containing 1, 2 or 3 heteroatoms independently selected from oxygen, nitrogen and sulphur (preferably nitrogen), and wherein the heteroaryl is independently unsubstituted or mono- or di-substituted, wherein the substituents are independently selected from the group consisting of $(C_{1-4})$alkyl; $(C_{3-6})$cycloalkyl; $(C_{1-4})$alkoxy; $(C_{1-2})$alkoxy-$(C_{1-2})$alkyl; $(C_{1-2})$alkyl-carbonyl; hydroxy-$(C_{1-4})$alkyl; halogen; $(C_{1-2})$fluoroalkyl; phenyl; and heteroaryl, wherein the heteroaryl is a 5- or 6-membered monocyclic aromatic ring containing 1, 2 or 3 heteroatoms independently selected from oxygen, nitrogen and sulphur (preferably oxygen and nitrogen), and wherein the heteroaryl is independently unsubstituted or mono-substituted with $(C_{1-4})$alkyl; and
$R^2$ represents $(C_{3-6})$cycloalkyl, $(C_{1-4})$alkoxy or $(C_{1-2})$fluoroalkyl;
and to the salts (in particular pharmaceutically acceptable salts) of such compounds.

Definitions provided herein are intended to apply uniformly to the compounds of Formulae (I), $(I_{TA})$, $(I_{St1})$ and $(I_{St2})$ as defined in any one of embodiments 1) to 24), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) as defined in any one of embodiments 1) to 24), may contain one or more stereogenic or asymmetric centers, such as one or more asymmetric carbon atoms. The compounds of Formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers, is understood in the context of the present invention to mean especially that the respective enantiomer is present in a ratio (mutatis mutandis: purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The term "halogen" means fluorine, chlorine, bromine or iodine. In case a "halogen" is a substituent to a "heteroaryl group" representing "$R^1$", the term "halogen" means preferably fluorine or chlorine, and more preferably fluorine.

The term "alkyl", used alone or in combination, refers to a straight or branched saturated hydrocarbon chain containing one to four carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, n-propyl, iso-propyl, n-butyl, iso-butyl, sec.-butyl and tert.-butyl. Examples of $(C_{1-3})$alkyl groups are methyl, ethyl, n-propyl and iso-propyl. Examples of $(C_{1-2})$alkyl groups are methyl and ethyl. In case a "$(C_{x-y})$alkyl" group is a substituent to a "heteroaryl group" representing "$R^1$", the term "$(C_{x-y})$alkyl" means methyl, ethyl, n-propyl, iso-propyl, n-butyl, iso-butyl, sec.-butyl and tert.-butyl and preferably methyl, ethyl, iso-propyl and tert.-butyl. In case a "$(C_{x-y})$alkyl" group is a substituent to a "heteroaryl group" being itself a substituent to a "heteroaryl group" representing "$R^1$" (or in case a "$(C_{x-y})$alkyl" group is a substituent to a "heteroaryl group" representing "$R^{1A}$"), the term "$(C_{x-y})$alkyl" means methyl, ethyl, n-propyl, iso-propyl, n-butyl, iso-butyl, sec.-butyl and tert.-butyl and preferably methyl. In case $R^{1A}$ represents "$(C_{x-y})$alkyl" the term means methyl, ethyl, n-propyl, iso-propyl, n-butyl, iso-butyl, sec.-butyl and tert.-butyl; preferably methyl, ethyl, iso-propyl and tert.-butyl; and more preferably methyl, ethyl and iso-propyl. In case $R^{1B}$ represents "$(C_{x-y})$alkyl" the term means methyl, ethyl, n-propyl, iso-propyl, n-butyl, iso-butyl, sec.-butyl and tert.-butyl; preferably methyl and ethyl; and more preferably methyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, iso-propoxy, n-butoxy, iso-butoxy, sec.-butoxy and tert.-butoxy. Examples of $(C_{1-2})$alkoxy groups are methoxy and ethoxy. In case a "$(C_{x-y})$alkoxy" group is a substituent to a "heteroaryl group" representing "$R^1$", the term "$(C_{x-y})$alkoxy" means methoxy, ethoxy, n-propoxy, iso-propoxy, n-butoxy, iso-butoxy, sec.-butoxy and tert.-butoxy and preferably methoxy. In case $R^2$ represents "$(C_{x-y})$alkoxy" the term means methoxy, ethoxy, n-propoxy, iso-propoxy, n-butoxy, iso-butoxy, sec.-butoxy and tert.-butoxy and preferably ethoxy.

The term "hydroxy-$(C_{1-4})$alkyl", used alone or in combination, refers to an alkyl group as defined before containing from one to four carbon atoms in which one hydrogen atom has been replaced with hydroxy. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. In case a "hydroxy-$(C_{1-4})$alkyl" group is a substituent to a "heteroaryl group" representing "$R^1$" (or in case "$R^{1A}$" represents "hydroxy-$(C_{1-4})$alkyl"), the term "hydroxy-$(C_{1-4})$alkyl" means hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. Preferred are hydroxy-methyl and 1-hydroxy-ethyl and more preferred is 1-hydroxy-ethyl.

The term "$(C_{xa-ya})$alkoxy-$(C_{x-y})$alkyl" (x, xa, y and ya each being an integer) refers to an alkyl group as defined before containing x to y carbon atoms wherein one hydrogen atom has been replaced with $(C_{xa-ya})$alkoxy as defined before containing xa to ya carbon atoms. For example a "$(C_{1-2})$alkoxy-$(C_{1-2})$alkyl group" refers to an $(C_{1-2})$alkyl group as defined before containing one or two carbon atoms wherein one hydrogen atom has been replaced with $(C_{1-2})$alkoxy as defined before containing one or two carbon atoms. Examples of $(C_{1-2})$alkoxy-$(C_{1-2})$alkyl groups are methoxy-methyl, 1-methoxy-ethyl, 2-methoxy-ethyl, ethoxy-methyl, 1-ethoxy-ethyl and 2-ethoxy-ethyl. In case a "$(C_{1-2})$alkoxy-$(C_{1-2})$alkyl" group is a substituent to a "heteroaryl group" representing "$R^1$" (or in case "$R^{1A}$" represents "$(C_{1-2})$alkoxy-$(C_{1-2})$alkyl"), the term "$(C_{1-2})$alkoxy-$(C_{1-2})$alkyl" means methoxy-methyl, 1-methoxy-ethyl, 2-methoxy-ethyl, ethoxy-methyl, 1-ethoxy-ethyl and 2-ethoxy-ethyl and preferably methoxy-methyl.

The term "fluoroalkyl" refers to an alkyl group as defined before containing one or two carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-2})$fluoroalkyl group contains one or two carbon atoms in which one to five hydrogen atoms have been replaced with fluorine. Representative examples of $(C_{1-2})$fluoroalkyl groups include fluoromethyl, difluoromethyl, trifluoromethyl, 1-fluoroethyl, 1,1-difluoroethyl, 2-fluoroethyl, 2,2-difluoroethyl, and 2,2,2-trifluoroethyl. In case a "$(C_{x-y})$fluoroalkyl" group is a substituent to a "heteroaryl group" representing "$R^1$" (or in case "$R^{1A}$" represents "$(C_{x-y})$fluoroalkyl"), the term "$(C_{x-y})$fluoroalkyl" means preferably fluoromethyl, difluoromethyl, trifluoromethyl, 1-fluoroethyl, 1,1-difluoroethyl, 2-fluoroethyl, 2,2-difluoroethyl, and 2,2,2-trifluoroethyl and more preferably difluoromethyl and trifluoromethyl. In case $R^2$ represents "$(C_{x-y})$fluoroalkyl" the term means preferably fluoromethyl, difluoromethyl, trifluoromethyl, 1-fluoroethyl, 1,1-difluoroethyl, 2-fluoroethyl, 2,2-difluoroethyl, and 2,2,2-trifluoroethyl and more preferably trifluoromethyl.

The term "$(C_{x-y})$alkyl-carbonyl" (x and y each being an integer) refers to an alkyl group as defined before containing x to y carbon atoms which is attached to the rest of the molecule via a carbonyl group. For example a $(C_{1-2})$alkyl-carbonyl group contains in the alkyl moiety one or two carbon atoms and is attached to the rest of the molecule via a carbonyl group. Examples of "$(C_{1-2})$alkyl-carbonyl" groups are methyl-carbonyl and ethyl-carbonyl. In case a "$(C_{1-2})$alkyl-carbonyl" group is a substituent to a "heteroaryl group" representing "$R^1$" (or in case "$R^{1A}$" represents "$(C_{1-2})$alkyl-carbonyl"), the term "$(C_{1-2})$alkyl-carbonyl" means methyl-carbonyl and ethyl-carbonyl and preferably methyl-carbonyl (acetyl).

The term "cycloalkyl", used alone or in combination, refers to a saturated carbocyclic ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of $(C_{3-6})$cycloalkyl groups are cyclopropyl, cyclobutyl, cyclopentyl, and cyclohexyl. In case a "$(C_{3-6})$cycloalkyl" group is a substituent to a "heteroaryl group" representing "$R^1$" (or in case "$R^{1A}$" represents "$(C_{3-6})$cycloalkyl"), the term "$(C_{3-6})$cycloalkyl" means cyclopropyl, cyclobutyl, cyclopentyl and cyclohexyl, preferably cyclopropyl and cyclobutyl and more preferably cyclopropyl. In case "$R^2$" represents "$(C_{3-6})$cycloalkyl" the term means cyclopropyl, cyclobutyl, cyclopentyl and cyclohexyl and preferably cyclopropyl.

The term "heteroaryl", used alone or in combination, refers to a heteroaryl-group as specifically defined which group may be unsubstituted or substituted as specifically defined. Examples of "heteroaryl groups, wherein the heteroaryl is a 5- to 10-membered monocyclic or bicyclic aromatic ring containing 1, 2 or 3 heteroatoms independently selected from oxygen, nitrogen and sulphur" are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, triazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, and imidazopyridinyl. In case of an heteroaryl group having a more restricted definition, the list of examples may be construed from the aforementioned list by taking the respective restrictions into account. For instance, examples of "heteroaryl groups, wherein the heteroaryl is a 5- or 6-membered monocyclic aromatic ring containing 1, 2 or 3 heteroatoms independently selected from oxygen, nitrogen and sulphur" are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, and triazinyl. Preferred examples of "heteroaryl-groups" representing "$R^1$" are pyrazolyl (notably pyrazol-1-yl), triazolyl (notably [1,2,4]triazol-1-yl), indolyl (notably indol-1-yl), benzimidazolyl (notably benzimidazol-1-yl) and imidazo[4,5-b]pyridinyl (notably imidazo[4,5-b]pyridin-3-yl) and most preferred is [1,2,4]triazol-1-yl; the heteroaryl group may be unsubstituted or substituted as specifically defined; preferred examples of "unsubstituted or substituted heteroaryl-groups" representing "$R^1$" are 3-methyl-pyrazol-1-yl, 3-methyl-[1,2,4]triazol-1-yl, 3-ethyl-[1,2,4]triazol-1-yl, 3-isopropyl-[1,2,4]triazol-1-yl, 3-tert.-butyl-[1,2,4]triazol-1-yl, 3-cyclopropyl-[1,2,4]triazol-1-yl, 3-cyclobutyl-[1,2,4]triazol-1-yl, 3-methoxymethyl-[1,2,4]triazol-1-yl, 3-acetyl-[1,2,4]triazol-1-yl, 3-(1-hydroxy-ethyl)-[1,2,4]triazol-1-yl, 3-difluoromethyl-[1,2,4]triazol-1-yl, 3-trifluoromethyl-[1,2,4]triazol-1-yl, 3-phenyl-[1,2,4]triazol-1-yl, 3-(5-methyl-[1,2,4]oxadiazol-3-yl)-[1,2,4]triazol-1-yl, 3-(pyridin-2-yl)-[1,2,4]triazol-1-yl, 5-methyl-[1,2,4]triazol-1-yl, 5-ethyl-[1,2,4]triazol-1-yl, 3,5-dimethyl-[1,2,4]triazol-1-yl, 3-ethyl-5-methyl-[1,2,4]triazol-1-yl, 5-ethyl-3-methyl-[1,2,4]triazol-1-yl, 5-methoxy-indol-1-yl, 5-fluoro-indol-1-yl, benzimidazol-1-yl and imidazo[4,5-b]pyridin-3-yl. Further examples are 3-ethyl-pyrazol-1-yl and 3-cyclopropyl-pyrazol-1-yl. Preferred examples of "heteroaryl-groups" being a substituent to a heteroaryl group representing "$R^1$" (or of "heteroaryl-groups" representing "$R^{1,4}$") are oxadiazolyl (notably [1,2,4]oxadiazol-3-yl) and pyridinyl (notably pyridin-2-yl); the heteroaryl group may be unsubstituted or substituted as specifically defined; preferred examples of "unsubstituted or substituted heteroaryl-groups" being a substituent to a heteroaryl group representing "$R^1$" (or of "unsubstituted or substituted heteroaryl-groups" representing "$R^{1,4}$") are 5-methyl-[1,2,4]oxadiazol-3-yl and pyridin-2-yl.

2) A further embodiment of the invention relates to compounds of Formula (I) according to embodiment 1), wherein
n represents the integer 1 or 2;
X represents N;
$R^1$ represents heteroaryl, wherein the heteroaryl is a 5- to 10-membered monocyclic or bicyclic aromatic ring containing 1, 2 or 3 nitrogen atoms, and wherein the heteroaryl is independently unsubstituted or mono- or di-substituted, wherein the substituents are independently selected from the group consisting of ($C_{1-4}$)alkyl; ($C_{3-6}$)cycloalkyl; ($C_{1-4}$)alkoxy; ($C_{1-2}$)alkoxy-($C_{1-2}$)alkyl; ($C_{1-2}$)alkyl-carbonyl; hydroxy-($C_{1-4}$)alkyl; halogen; and ($C_{1-2}$)fluoroalkyl; and
$R^2$ represents ($C_{3-6}$)cycloalkyl, ($C_{1-4}$)alkoxy or ($C_{1-2}$)fluoroalkyl;
and to the salts (in particular pharmaceutically acceptable salts) of such compounds.

3) A further embodiment of the invention relates to compounds of Formula (I) according to embodiment 1), wherein
n represents the integer 1 or 2;
X represents N;
$R^1$ represents a 5-membered monocyclic heteroaryl group containing 2 or 3 nitrogen atoms which is independently mono- or di-substituted, wherein the substituents are independently selected from the group consisting of ($C_{1-4}$)alkyl, ($C_{3-6}$)cycloalkyl, ($C_{1-2}$)alkoxy-($C_{1-2}$)alkyl, hydroxy-($C_{1-4}$)alkyl and ($C_{1-2}$)fluoroalkyl; or a 9-membered bicyclic aromatic ring containing 1, 2 or 3 nitrogen atoms which is unsubstituted or mono-substituted with ($C_{1-4}$)alkoxy or halogen; and
$R^2$ represents ($C_{3-6}$)cycloalkyl, ($C_{1-4}$)alkoxy or trifluoromethyl;
and to the salts (in particular pharmaceutically acceptable salts) of such compounds.

4) A further embodiment of the invention relates to compounds of Formula (I) according to any one of embodiments 1) to 3), wherein
n represents the integer 1;
and to the salts (in particular pharmaceutically acceptable salts) of such compounds.

5) A further embodiment of the invention relates to compounds of Formula (I) according to any one of embodiments 1) to 3), wherein
n represents the integer 2;
and to the salts (in particular pharmaceutically acceptable salts) of such compounds.

6) A further embodiment of the invention relates to compounds of Formula (I) according to any one of embodiments 1) to 5), wherein
$R^1$ represents a 5-membered monocyclic heteroaryl group containing 2 or 3 nitrogen atoms which is independently mono- or di-substituted, wherein the substituents are independently selected from the group consisting of ($C_{1-4}$)alkyl, ($C_{3-6}$)cycloalkyl and ($C_{1-2}$)fluoroalkyl; and to the salts (in particular pharmaceutically acceptable salts) of such compounds.

7) A further embodiment of the invention relates to compounds of Formula (I) according to any one of embodiments 1) to 6), wherein
$R^2$ represents trifluoromethyl;
and to the salts (in particular pharmaceutically acceptable salts) of such compounds.

8) A further embodiment of the invention relates to compounds of Formula (I) according to embodiment 1) which are also compounds of Formula ($I_{T4}$)

Formula ($I_{TA}$)

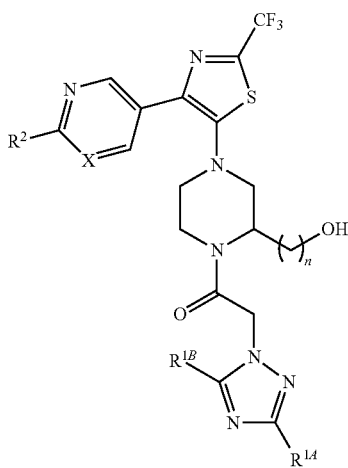

wherein
n represents the integer 1 or 2;
$R^{1A}$ represents hydrogen, $(C_{1-4})$alkyl, $(C_{3-6})$cycloalkyl, $(C_{1-2})$alkoxy-$(C_{1-2})$alkyl, $(C_{1-2})$alkyl-carbonyl, hydroxy-$(C_{1-4})$alkyl, $(C_{1-2})$fluoroalkyl, phenyl or heteroaryl, wherein the heteroaryl is a 5- or 6-membered monocyclic aromatic ring containing 1, 2 or 3 heteroatoms independently selected from oxygen, nitrogen and sulphur (preferably oxygen and nitrogen), and wherein the heteroaryl is independently unsubstituted or mono-substituted with $(C_{1-4})$alkyl;
$R^{1B}$ represents hydrogen or $(C_{1-4})$alkyl; and
$R^2$ represents $(C_{3-6})$cycloalkyl, $(C_{1-4})$alkoxy or $(C_{1-2})$fluoroalkyl;
and to the salts (in particular pharmaceutically acceptable salts) of such compounds.

9) A further embodiment of the invention relates to compounds of Formula ($I_{TA}$) according to embodiment 8), wherein
n represents the integer 1 or 2;
$R^{1A}$ represents $(C_{1-4})$alkyl, $(C_{3-6})$cycloalkyl, $(C_{1-2})$alkoxy-$(C_{1-2})$alkyl, $(C_{1-2})$alkyl-carbonyl, hydroxy-$(C_{1-4})$alkyl or $(C_{1-2})$fluoroalkyl; and $R^{1B}$ represents hydrogen or $(C_{1-4})$alkyl; or
$R^{1A}$ represents hydrogen and $R^{1B}$ represents $(C_{1-4})$alkyl; and
$R^2$ represents $(C_{3-6})$cycloalkyl, $(C_{1-4})$alkoxy or $(C_{1-2})$fluoroalkyl;
and to the salts (in particular pharmaceutically acceptable salts) of such compounds.

10) A further embodiment of the invention relates to compounds of Formula ($I_{TA}$) according to embodiment 8), wherein
n represents the integer 1 or 2;
$R^{1A}$ represents $(C_{1-4})$alkyl or $(C_{3-6})$cycloalkyl;
$R^{1B}$ represents hydrogen or $(C_{1-4})$alkyl; and
$R^2$ represents cyclopropyl, ethoxy or trifluoromethyl;
and to the salts (in particular pharmaceutically acceptable salts) of such compounds.

11) A further embodiment of the invention relates to compounds of Formula ($I_{TA}$) according to any one of embodiments 8) to 10), wherein
n represents the integer 1;
and to the salts (in particular pharmaceutically acceptable salts) of such compounds.

12) A further embodiment of the invention relates to compounds of Formula ($I_{TA}$) according to any one of embodiments 8) to 10), wherein
n represents the integer 2;
and to the salts (in particular pharmaceutically acceptable salts) of such compounds.

13) A further embodiment of the invention relates to compounds of Formula ($I_{TA}$) according to any one of embodiments 8), 9), 11) or 12), wherein
$R^{1A}$ represents $(C_{1-4})$alkyl, $(C_{3-6})$cycloalkyl, $(C_{1-2})$alkoxy-$(C_{1-2})$alkyl, hydroxy-$(C_{1-4})$alkyl or $(C_{1-2})$fluoroalkyl;
and to the salts (in particular pharmaceutically acceptable salts) of such compounds.

14) A further embodiment of the invention relates to compounds of Formula ($I_{TA}$) according to any one of embodiments 8), 9), 11) or 12), wherein
$R^{1A}$ represents $(C_{1-4})$alkyl or $(C_{3-6})$cycloalkyl;
and to the salts (in particular pharmaceutically acceptable salts) of such compounds.

15) A further embodiment of the invention relates to compounds of Formula ($I_{TA}$) according to any one of embodiments 8) to 12), wherein
$R^{1A}$ represents methyl, ethyl, iso-propyl or cyclopropyl;
and to the salts (in particular pharmaceutically acceptable salts) of such compounds.

16) A further embodiment of the invention relates to compounds of Formula ($I_{TA}$) according to any one of embodiments 8) to 15), wherein
$R^{1B}$ represents hydrogen;
and to the salts (in particular pharmaceutically acceptable salts) of such compounds.

17) A further embodiment of the invention relates to compounds of Formula ($I_{TA}$) according to any one of embodiments 8) to 15), wherein
$R^{1B}$ represents methyl;
and to the salts (in particular pharmaceutically acceptable salts) of such compounds.

18) A further embodiment of the invention relates to compounds of Formula ($I_{TA}$) according to any one of embodiments 8), 9) or 11) to 17), wherein
$R^2$ represents $(C_{1-4})$alkoxy or $(C_{1-2})$fluoroalkyl;
and to the salts (in particular pharmaceutically acceptable salts) of such compounds.

19) A further embodiment of the invention relates to compounds of Formula ($I_{TA}$) according to any one of embodiments 8) to 17), wherein
$R^2$ represents trifluoromethyl;
and to the salts (in particular pharmaceutically acceptable salts) of such compounds.

20) A further embodiment of the invention relates to compounds according to any one of embodiments 1) to 19), wherein the absolute configuration of the stereogenic center is as depicted in formula ($I_{St1}$)

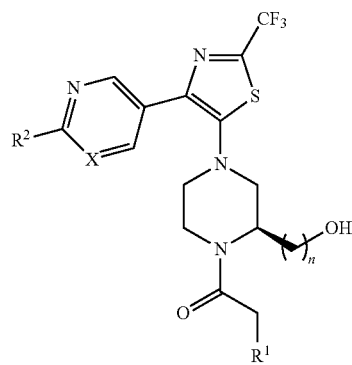

and to the salts (in particular pharmaceutically acceptable salts) of such compounds.

21) A further embodiment of the invention relates to compounds according to any one of embodiments 1) to 19), wherein the absolute configuration of the stereogenic center is as depicted in formula (I$_{St2}$)

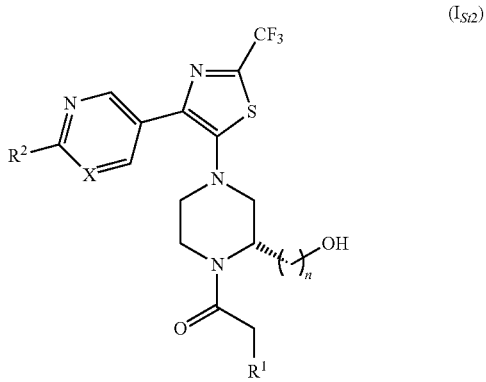

(I$_{St2}$)

and to the salts (in particular pharmaceutically acceptable salts) of such compounds.

22) Examples of compounds of Formula (I) as defined in embodiment 1) are selected from the group consisting of:
2-(3-tert-Butyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;
2-(3,5-Dimethyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;
2-(3-Cyclopropyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;
1-{(S)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;
1-{(S)-2-Hydroxymethyl-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone;
1-{(S)-4-[4-(2-Ethoxy-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone;
2-(3,5-Dimethyl-[1,2,4]triazol-1-yl)-1-{(S)-4-[4-(2-ethoxy-pyrimidin-5-yl)-2-trifluoromethyl-thiazol-5-yl]-2-hydroxymethyl-piperazin-1-yl}-ethanone;
1-{(S)-4-[4-(2-Cyclopropyl-pyrimidin-5-yl)-2-trifluoromethyl-thiazol-5-yl]-2-hydroxymethyl-piperazin-1-yl}-2-(3,5-dimethyl-[1,2,4]triazol-1-yl)-ethanone;
1-{(S)-4-[4-(2-Cyclopropyl-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone;
1-{(R)-2-Hydroxymethyl-4-[2-trifluoromethyl-4-(6-trifluoromethyl-pyridin-3-yl)-thiazol-5-yl]-piperazin-1-yl}-2-(3-isopropyl-[1,2,4]triazol-1-yl)-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;
2-(3,5-Dimethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;
2-Benzoimidazol-1-yl-1-{(R)-2-hydroxymethyl-4-[2-trifluoromethyl-4-(2-trifluoromethyl-pyrimidin-5-yl)-thiazol-5-yl]-piperazin-1-yl}-ethanone;
2-(5-Fluoro-indol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(5-methoxy-indol-1-yl)-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-[3-(5-methyl-[1,2,4]oxadiazol-3-yl)-[1,2,4]triazol-1-yl]-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-phenyl-[1,2,4]triazol-1-yl)-ethanone;
2-(3-Acetyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;
2-[3-(1-Hydroxy-ethyl)-[1,2,4]triazol-1-yl]-1-{(R)-2-hydroxymethyl-4-[2-trifluoromethyl-4-(2-trifluoromethyl-pyrimidin-5-yl)-thiazol-5-yl]-piperazin-1-yl}-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-(3-pyridin-2-yl-[1,2,4]triazol-1-yl)-ethanone;
2-(3-Ethyl-5-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;
2-(5-Ethyl-3-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;
1-{(R)-2-Hydroxymethyl-4-[2-trifluoromethyl-4-(2-trifluoromethyl-pyrimidin-5-yl)-thiazol-5-yl]-piperazin-1-yl}-2-imidazo[4,5-b]pyridin-3-yl-ethanone;
2-(3,5-Dimethyl-[1,2,4]triazol-1-yl)-1-{(R)-2-(2-hydroxyethyl)-4-[2-trifluoromethyl-4-(2-trifluoromethyl-pyrimidin-5-yl)-thiazol-5-yl]-piperazin-1-yl}-ethanone;
1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone;
2-(3-Cyclobutyl-[1,2,4]triazol-1-yl)-1-{(R)-2-(2-hydroxyethyl)-4-[2-trifluoromethyl-4-(2-trifluoromethyl-pyrimidin-5-yl)-thiazol-5-yl]-piperazin-1-yl}-ethanone;
2-(3-tert-Butyl-[1,2,4]triazol-1-yl)-1-{(R)-2-(2-hydroxyethyl)-4-[2-trifluoromethyl-4-(2-trifluoromethyl-pyrimidin-5-yl)-thiazol-5-yl]-piperazin-1-yl}-ethanone;
2-(3-Cyclopropyl-[1,2,4]triazol-1-yl)-1-{(R)-2-(2-hydroxyethyl)-4-[2-trifluoromethyl-4-(2-trifluoromethyl-pyrimidin-5-yl)-thiazol-5-yl]-piperazin-1-yl}-ethanone;
2-(3-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;
2-(5-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;
1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;
1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(5-methyl-[1,2,4]triazol-1-yl)-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone; and 2-(3-Difluoromethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

or salts (in particular pharmaceutically acceptable salts) of such compounds.

23) Further examples of compounds of Formula (I) as defined in embodiment 1) are selected from the group consisting of:

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

2-(3-Ethyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(3-Cyclopropyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

1-{(S)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

2-(3-Ethyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone; and 2-(3-Cyclopropyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;

or salts (in particular pharmaceutically acceptable salts) of such compounds.

24) The invention, thus, relates to compounds of the Formula (I) as defined in embodiment 1), compounds of the Formula ($I_{TA}$) as defined in embodiment 8), compounds of the Formula ($I_{Sr1}$) as defined in embodiment 20), compounds of the Formula ($I_{Sr2}$) as defined in embodiment 21), and to such compounds further limited by the characteristics of any one of embodiments 2) to 7), 9) to 19), 22) and 23), all under consideration of their respective dependencies; to pharmaceutically acceptable salts thereof; and to the use of such compounds as medicaments especially in the treatment of disorders relating to a dysfunction of the CXCR3 receptor or dysfunction of ligands signalling through CXCR3, such as especially autoimmune disorders, inflammatory diseases, infectious diseases, transplant rejection, fibrosis, neurodegenerative disorders and cancer. Especially the following embodiments relating to the compounds of formulae (I), ($I_{TA}$), ($I_{Sr1}$) and ($I_{Sr2}$) are thus possible and intended and herewith specifically disclosed in individualized form: 1, 2+1, 3+1, 4+1, 4+2+1, 4+3+1, 5+1, 5+2+1, 5+3+1, 6+1, 6+2+1, 6+3+1, 6+4+1, 6+4+2+1, 6+4+3+1, 6+5+1, 6+5+2+1, 6+5+3+1, 7+1, 7+2+1, 7+3+1, 7+4+1, 7+4+2+1, 7+4+3+1, 7+5+1, 7+5+2+1, 7+5+3+1, 7+6+1, 7+6+2+1, 7+6+3+1, 7+6+4+1, 7+6+4+2+1, 7+6+4+3+1, 7+6+5+1, 7+6+5+2+1, 7+6+5+3+1, 8+1, 9+8+1, 10+8+1, 11+8+1, 11+9+8+1, 11+10+8+1, 12+8+1, 12+9+8+1, 12+10+8+1, 13+8+1, 13+9+8+1, 13+11+8+1, 13+11+9+8+1, 13+11+10+8+1, 13+12+8+1, 13+12+9+8+1, 13+12+10+8+1, 14+8+1, 14+9+8+1, 14+11+8+1, 14+11+9+8+1, 14+11+10+8+1, 14+12+8+1, 14+12+9+8+1, 14+12+10+8+1, 15+8+1, 15+9+8+1, 15+10+8+1, 15+11+8+1, 15+11+9+8+1, 15+11+10+8+1, 15+12+8+1, 15+12+9+8+1, 15+12+10+8+1, 16+8+1, 16+9+8+1, 16+10+8+1, 16+11+8+1, 16+11+9+8+1, 16+11+10+8+1, 16+12+8+1, 16+12+9+8+1, 16+12+10+8+1, 16+13+8+1, 16+13+9+8+1, 16+13+11+8+1, 16+13+11+9+8+1, 16+13+11+10+8+1, 16+13+12+8+1, 16+13+12+9+8+1, 16+13+12+10+8+1, 16+14+8+1, 16+14+9+8+1, 16+14+11+8+1, 16+14+11+9+8+1, 16+14+11+10+8+1, 16+14+12+8+1, 16+14+12+9+8+1, 16+14+12+10+8+1, 16+15+8+1, 16+15+9+8+1, 16+15+10+8+1, 16+15+11+8+1, 16+15+11+9+8+1, 16+15+11+10+8+1, 16+15+12+8+1, 16+15+12+9+8+1, 16+15+12+10+8+1, 17+8+1, 17+9+8+1, 17+10+8+1, 17+11+8+1, 17+11+9+8+1, 17+11+10+8+1, 17+12+8+1, 17+12+9+8+1, 17+12+10+8+1, 17+13+8+1, 17+13+9+8+1, 17+13+11+8+1, 17+13+11+9+8+1, 17+13+11+10+8+1, 17+13+12+8+1, 17+13+12+9+8+1, 17+13+12+10+8+1, 17+14+8+1, 17+14+9+8+1, 17+14+11+8+1, 17+14+11+9+8+1, 17+14+11+10+8+1, 17+14+12+8+1, 17+14+12+9+8+1, 17+14+12+10+8+1, 17+15+8+1, 17+15+9+8+1, 17+15+10+8+1, 17+15+11+8+1, 17+15+11+9+8+1, 17+15+11+10+8+1, 17+15+12+8+1 17+15+12+9+8+1, 17+15+12+10+8+1, 18+8+1, 18+9+8+1, 18+11+8+1, 18+11+9+8+1, 18+11+10+8+1, 18+12+8+1, 18+12+9+8+1, 18+12+10+8+1, 18+13+8+1, 18+13+9+8+1, 18+13+11+8+1, 18+13+11+9+8+1, 18+13+11+10+8+1, 18+13+12+8+1, 18+13+12+9+8+1, 18+13+12+10+8+1, 18+14+8+1, 18+14+9+8+1, 18+14+11+8+1, 18+14+11+9+8+1, 18+14+11+10+8+1, 18+14+12+8+1, 18+14+12+9+8+1, 18+14+12+10+8+1, 18+15+8+1, 18+15+9+8+1, 18+15+10+8+1, 18+15+11+8+1, 18+15+11+9+8+1, 18+15+11+10+8+1, 18+15+12+8+1, 18+15+12+9+8+1, 18+15+12+10+8+1, 18+16+8+1, 18+16+9+8+1, 18+16+10+8+1, 18+16+11+8+1, 18+16+11+9+8+1, 18+16+11+10+8+1, 18+16+12+8+1, 18+16+12+9+8+1, 18+16+12+10+8+1, 18+16+13+8+1, 18+16+13+9+8+1, 18+16+13+11+8+1, 18+16+13+11+9+8+1, 18+16+13+11+10+8+1, 18+16+13+12+8+1, 18+16+13+12+9+8+1, 18+16+13+12+10+8+1, 18+16+14+8+1, 18+16+14+9+8+1, 18+16+14+11+8+1, 18+16+14+11+9+8+1, 18+16+14+11+10+8+1, 18+16+14+12+8+1, 18+16+14+12+9+8+1, 18+16+14+12+10+8+1, 18+16+15+8+1, 18+16+15+9+8+1, 18+16+15+10+8+1, 18+16+15+11+8+1, 18+16+15+11+9+8+1, 18+16+15+11+10+8+1, 18+16+15+12+8+1, 18+16+15+12+9+8+1, 18+16+15+12+10+8+1, 18+17+8+1, 18+17+9+8+1, 18+17+10+8+1, 18+17+11+8+1, 18+17+11+9+8+1, 18+17+11+10+8+1, 18+17+12+8+1, 18+17+12+9+8+1, 18+17+12+10+8+1, 18+17+13+8+1, 18+17+13+9+8+1, 18+17+13+11+8+1, 18+17+13+11+9+8+1, 18+17+13+11+10+8+1, 18+17+13+12+8+1, 18+17+13+12+9+8+1, 18+17+13+12+10+8+1, 18+17+14+8+1, 18+17+14+9+8+1, 18+17+14+11+8+1, 18+17+14+11+9+8+1, 18+17+14+11+10+8+1, 18+17+14+12+8+1, 18+17+14+12+9+8+1, 18+17+14+12+10+8+1, 18+17+15+8+1, 18+17+15+9+8+1, 18+17+15+10+8+1, 18+17+15+11+8+1, 18+17+15+11+9+8+1, 18+17+15+11+10+8+1, 18+17+15+12+8+1, 18+17+15+12+9+8+1, 18+17+15+12+10+8+1, 19+8+1, 19+9+8+1, 19+10+8+1, 19+11+8+1, 19+11+9+8+1, 19+11+10+8+1, 19+12+8+1, 19+12+9+8+1, 19+12+10+8+1, 19+13+8+1, 19+13+9+8+1, 19+13+11+8+1, 19+13+11+9+8+1, 19+13+11+10+8+1, 19+13+12+8+1, 19+13+12+9+8+1, 19+13+12+10+8+1, 19+14+8+1, 19+14+9+8+1, 19+14+11+8+1, 19+14+11+9+8+1, 19+14+11+10+8+1, 19+14+12+8+1, 19+14+12+9+8+1, 19+14+12+10+8+1, 19+15+8+1, 19+15+9+8+1, 19+15+10+8+1, 19+15+11+8+1, 19+15+11+9+8+1, 19+15+11+10+8+1, 19+15+12+8+1, 19+15+12+9+8+1, 19+15+12+10+8+1, 19+16+8+1, 19+16+9+8+1, 19+16+10+8+1, 19+16+11+8+1, 19+16+11+9+8+1, 19+16+11+10+8+1, 19+16+12+8+1, 19+16+12+9+8+1, 19+16+12+10+8+1, 19+16+13+8+1, 19+16+13+9+8+1, 19+16+13+11+8+1, 19+16+13+11+9+8+1, 19+16+13+11+10+8+1, 19+16+13+12+8+1, 19+16+13+

12+9+8+1, 19+16+13+12+10+8+1, 19+16+14+8+1, 19+16+14+9+8+1, 19+16+14+11+8+1, 19+16+14+11+9+8+1, 19+16+14+11+10+8+1, 19+16+14+12+8+1, 19+16+14+12+9+8+1, 19+16+14+12+10+8+1, 19+16+15+8+1, 19+16+15+9+8+1, 19+16+15+10+8+1, 19+16+15+11+8+1, 19+16+15+11+9+8+1, 19+16+15+11+10+8+1, 19+16+15+12+8+1, 19+16+15+12+9+8+1, 19+16+15+12+10+8+1, 19+17+8+1, 19+17+9+8+1, 19+17+10+8+1, 19+17+11+8+1, 19+17+11+9+8+1, 19+17+11+10+8+1, 19+17+12+8+1, 19+17+12+9+8+1, 19+17+12+10+8+1, 19+17+13+8+1, 19+17+13+9+8+1, 19+17+13+11+8+1, 19+17+13+11+9+8+1, 19+17+13+11+10+8+1, 19+17+13+12+8+1, 19+17+13+12+9+8+1, 19+17+13+12+10+8+1, 19+17+14+8+1, 19+17+14+9+8+1, 19+17+14+11+8+1, 19+17+14+11+9+8+1, 19+17+14+11+10+8+1, 19+17+14+12+8+1, 19+17+14+12+9+8+1, 19+17+14+12+10+8+1, 19+17+15+8+1, 19+17+15+9+8+1, 19+17+15+10+8+1, 19+17+15+11+8+1, 19+17+15+11+9+8+1, 19+17+15+11+10+8+1, 19+17+15+12+8+1, 19+17+15+12+9+8+1, 19+17+15+12+10+8+1, 20+1, 20+2+1, 20+3+1, 20+4+1, 20+4+2+1, 20+4+3+1, 20+5+1, 20+5+2+1, 20+5+3+1, 20+6+1, 20+6+2+1, 20+6+3+1, 20+6+4+1, 20+6+4+2+1, 20+6+4+3+1, 20+6+5+1, 20+6+5+2+1, 20+6+5+3+1, 20+7+1, 20+7+2+1, 20+7+3+1, 20+7+4+1, 20+7+4+2+1, 20+7+4+3+1, 20+7+5+1, 20+7+5+2+1, 20+7+5+3+1, 20+7+6+1, 20+7+6+2+1, 20+7+6+3+1, 20+7+6+4+1, 20+7+6+4+2+1, 20+7+6+4+3+1, 20+7+6+5+1, 20+7+6+5+2+1, 20+7+6+5+3+1, 20+8+1, 20+9+8+1 20+10+8+1, 20+11+8+1, 20+11+9+8+1, 20+11+10+8+1, 20+12+8+1, 20+12+9+8+1, 20+12+10+8+1, 20+13+8+1, 20+13+9+8+1, 20+13+11+8+1, 20+13+11+9+8+1, 20+13+11+10+8+1, 20+13+12+8+1, 20+13+12+9+8+1, 20+13+12+10+8+1, 20+14+8+1, 20+14+9+8+1, 20+14+11+8+1, 20+14+11+9+8+1, 20+14+11+10+8+1, 20+14+12+8+1, 20+14+12+9+8+1, 20+14+12+10+8+1, 20+15+8+1, 20+15+9+8+1, 20+15+10+8+1, 20+15+11+8+1, 20+15+11+9+8+1, 20+15+11+10+8+1, 20+15+12+8+1, 20+15+12+9+8+1, 20+15+12+10+8+1, 20+16+8+1, 20+16+9+8+1, 20+16+10+8+1, 20+16+11+8+1, 20+16+11+9+8+1, 20+16+11+10+8+1, 20+16+12+8+1, 20+16+12+9+8+1, 20+16+12+10+8+1, 20+16+13+8+1, 20+16+13+9+8+1, 20+16+13+11+8+1, 20+16+13+11+9+8+1, 20+16+13+11+10+8+1, 20+16+13+12+8+1, 20+16+13+12+9+8+1, 20+16+13+12+10+8+1, 20+16+14+8+1, 20+16+14+9+8+1, 20+16+14+11+8+1, 20+16+14+11+9+8+1, 20+16+14+11+10+8+1, 20+16+14+12+8+1, 20+16+14+12+9+8+1, 20+16+14+12+10+8+1, 20+16+15+8+1, 20+16+15+9+8+1, 20+16+15+10+8+1, 20+16+15+11+8+1, 20+16+15+11+9+8+1, 20+16+15+11+10+8+1, 20+16+15+12+8+1, 20+16+15+12+9+8+1, 20+16+15+12+10+8+1, 20+17+8+1, 20+17+9+8+1, 20+17+10+8+1, 20+17+11+8+1, 20+17+11+9+8+1, 20+17+11+10+8+1, 20+17+12+8+1, 20+17+12+9+8+1, 20+17+12+10+8+1, 20+17+13+8+1, 20+17+13+9+8+1, 20+17+13+11+8+1, 20+17+13+11+9+8+1, 20+17+13+11+10+8+1, 20+17+13+12+8+1, 20+17+13+12+9+8+1, 20+17+13+12+10+8+1, 20+17+14+8+1, 20+17+14+9+8+1, 20+17+14+11+8+1, 20+17+14+11+9+8+1, 20+17+14+11+10+8+1, 20+17+14+12+8+1, 20+17+14+12+9+8+1, 20+17+14+12+10+8+1, 20+17+15+8+1, 20+17+15+9+8+1, 20+17+15+10+8+1, 20+17+15+11+8+1, 20+17+15+11+9+8+1, 20+17+15+11+10+8+1, 20+17+15+12+8+1, 20+17+15+12+9+8+1, 20+17+15+12+10+8+1, 20+18+8+1, 20+18+9+8+1, 20+18+11+8+1, 20+18+11+9+8+1, 20+18+11+10+8+1, 20+18+12+8+1, 20+18+12+9+8+1, 20+18+12+10+8+1, 20+18+13+8+1, 20+18+13+9+8+1, 20+18+13+11+8+1, 20+18+13+11+9+8+1, 20+18+13+11+10+8+1, 20+18+13+12+8+1, 20+18+13+12+9+8+1, 20+18+13+12+10+8+1, 20+18+14+8+1, 20+18+14+9+8+1, 20+18+14+11+8+1, 20+18+14+11+9+8+1, 20+18+14+11+10+8+1, 20+18+14+12+8+1, 20+18+14+12+9+8+1, 20+18+14+12+10+8+1, 20+18+15+8+1, 20+18+15+9+8+1, 20+18+15+10+8+1, 20+18+15+11+8+1, 20+18+15+11+9+8+1, 20+18+15+11+10+8+1, 20+18+15+12+8+1, 20+18+15+12+9+8+1, 20+18+15+12+10+8+1, 20+18+16+8+1, 20+18+16+9+8+1, 20+18+16+10+8+1, 20+18+16+11+8+1, 20+18+16+11+9+8+1, 20+18+16+11+10+8+1, 20+18+16+12+8+1, 20+18+16+12+9+8+1, 20+18+16+12+10+8+1, 20+18+16+13+8+1, 20+18+16+13+9+8+1, 20+18+16+13+11+8+1, 20+18+16+13+11+9+8+1, 20+18+16+13+11+10+8+1, 20+18+16+13+12+8+1, 20+18+16+13+12+9+8+1, 20+18+16+13+12+10+8+1, 20+18+16+14+8+1, 20+18+16+14+9+8+1, 20+18+16+14+11+8+1, 20+18+16+14+11+9+8+1, 20+18+16+14+11+10+8+1, 20+18+16+14+12+8+1, 20+18+16+14+12+9+8+1, 20+18+16+14+12+10+8+1, 20+18+16+15+8+1, 20+18+16+15+9+8+1, 20+18+16+15+10+8+1, 20+18+16+15+11+8+1, 20+18+16+15+11+9+8+1, 20+18+16+15+11+10+8+1, 20+18+16+15+12+8+1, 20+18+16+15+12+9+8+1, 20+18+16+15+12+10+8+1, 20+18+17+8+1, 20+18+17+9+8+1, 20+18+17+10+8+1, 20+18+17+11+8+1, 20+18+17+11+9+8+1, 20+18+17+11+10+8+1, 20+18+17+12+8+1, 20+18+17+12+9+8+1, 20+18+17+12+10+8+1, 20+18+17+13+8+1, 20+18+17+13+9+8+1, 20+18+17+13+11+8+1, 20+18+17+13+11+9+8+1, 20+18+17+13+11+10+8+1, 20+18+17+13+12+8+1, 20+18+17+13+12+9+8+1, 20+18+17+13+12+10+8+1, 20+18+17+14+8+1, 20+18+17+14+9+8+1, 20+18+17+14+11+8+1, 20+18+17+14+11+9+8+1, 20+18+17+14+11+10+8+1, 20+18+17+14+12+8+1, 20+18+17+14+12+9+8+1, 20+18+17+14+12+10+8+1, 20+18+17+15+8+1, 20+18+17+15+9+8+1, 20+18+17+15+10+8+1, 20+18+17+15+11+8+1, 20+18+17+15+11+9+8+1, 20+18+17+15+11+10+8+1, 20+18+17+15+12+8+1, 20+18+17+15+12+9+8+1, 20+18+17+15+12+10+8+1, 20+19+8+1, 20+19+9+8+1, 20+19+10+8+1, 20+19+11+8+1, 20+19+11+9+8+1, 20+19+11+10+8+1, 20+19+12+8+1, 20+19+12+9+8+1, 20+19+12+10+8+1, 20+19+13+8+1, 20+19+13+9+8+1, 20+19+13+11+8+1, 20+19+13+11+9+8+1, 20+19+13+11+10+8+1, 20+19+13+12+8+1, 20+19+13+12+9+8+1, 20+19+13+12+10+8+1, 20+19+14+8+1, 20+19+14+9+8+1, 20+19+14+11+8+1, 20+19+14+11+9+8+1, 20+19+14+11+10+8+1, 20+19+14+12+8+1, 20+19+14+12+9+8+1, 20+19+14+12+10+8+1, 20+19+15+8+1, 20+19+15+9+8+1, 20+19+15+10+8+1, 20+19+15+11+8+1, 20+19+15+11+9+8+1, 20+19+15+11+10+8+1, 20+19+15+12+8+1, 20+19+15+12+9+8+1, 20+19+15+12+10+8+1, 20+19+16+8+1, 20+19+16+9+8+1, 20+19+16+10+8+1, 20+19+16+11+8+1, 20+19+16+11+9+8+1, 20+19+16+11+10+8+1, 20+19+16+12+8+1, 20+19+16+12+9+8+1, 20+19+16+12+10+8+1, 20+19+16+13+8+1, 20+19+16+13+9+8+1, 20+19+16+13+11+8+1, 20+19+16+13+11+9+8+1, 20+19+16+13+11+10+8+1, 20+19+16+13+12+8+1, 20+19+16+13+12+9+8+1, 20+19+16+13+12+10+8+1, 20+19+16+14+8+1, 20+19+16+14+9+8+1, 20+19+16+14+11+8+1, 20+19+16+14+11+9+8+1, 20+19+16+14+11+10+8+1, 20+19+16+14+12+8+1, 20+19+16+14+12+9+8+1, 20+19+16+14+12+10+8+1, 20+19+16+15+8+1, 20+19+16+15+9+8+1, 20+19+16+15+10+8+1, 20+19+16+15+11+8+1, 20+19+16+15+11+9+8+1, 20+19+16+15+11+10+8+1, 20+19+16+15+12+8+1, 20+19+16+15+12+9+8+1, 20+19+16+15+12+10+8+1, 20+19+17+8+1, 20+19+17+9+8+1, 20+19+17+10+8+1, 20+19+17+11+8+1, 20+19+17+11+9+8+1, 20+19+17+11+10+8+1, 20+19+17+12+8+1, 20+19+17+12+9+8+1, 20+19+17+12+10+8+1, 20+19+17+13+8+1, 20+19+17+13+9+8+1, 20+19+17+13+11+8+1, 20+19+17+13+11+9+8+1, 20+19+17+13+11+10+8+1, 20+19+17+13+12+8+1, 20+19+17+13+12+9+8+1, 20+19+

17+13+12+10+8+1, 20+19+17+14+8+1, 20+19+17+14+9+8+1, 20+19+17+14+11+8+1, 20+19+17+14+11+9+8+1, 20+19+17+14+11+10+8+1, 20+19+17+14+12+8+1, 20+19+17+14+12+9+8+1, 20+19+17+14+12+10+8+1, 20+19+17+15+8+1, 20+19+17+15+9+8+1, 20+19+17+15+10+8+1, 20+19+17+15+11+8+1, 20+19+17+15+11+9+8+1, 20+19+17+15+11+10+8+1, 20+19+17+15+12+8+1, 20+19+17+15+12+9+8+1, 20+19+17+15+12+10+8+1, 21+1, 21+2+1, 21+3+1, 21+4+1, 21+4+2+1, 21+4+3+1, 21+5+1, 21+5+2+1, 21+5+3+1, 21+6+1, 21+6+2+1, 21+6+3+1, 21+6+4+1, 21+6+4+2+1, 21+6+4+3+1, 21+6+5+1, 21+6+5+2+1, 21+6+5+3+1, 21+7+1, 21+7+2+1, 21+7+3+1, 21+7+4+1, 21+7+4+2+1, 21+7+4+3+1, 21+7+5+1, 21+7+5+2+1, 21+7+5+3+1, 21+7+6+1, 21+7+6+2+1, 21+7+6+3+1, 21+746+4+1, 21+7+6+4+2+1, 21+7+6+4+3+1, 21+7+6+5+1, 21+7+6+5+2+1, 21+7+6+5+3+1, 21+8+1, 21+9+8+1, 21+10+8+1, 21+11+8+1, 21+11+9+8+1, 21+11+10+8+1, 21+12+8+1, 21+12+9+8+1, 21+12+10+8+1, 21+13+8+1, 21+13+9+8+1, 21+13+11+8+1, 21+13+11+9+8+1, 21+13+11+10+8+1, 21+13+12+8+1, 21+13+12+9+8+1, 21+13+12+10+8+1, 21+14+8+1, 21+14+9+8+1, 21+14+11+8+1, 21+14+11+9+8+1, 21+14+11+10+8+1, 21+14+12+8+1, 21+14+12+9+8+1, 21+14+12+10+8+1, 21+15+8+1, 21+15+9+8+1, 21+15+10+8+1, 21+15+11+8+1, 21+15+11+9+8+1, 21+15+11+10+8+1, 21+15+12+8+1, 21+15+12+9+8+1, 21+15+12+10+8+1, 21+16+8+1, 21+16+9+8+1, 21+16+10+8+1, 21+16+11+8+1, 21+16+11+9+8+1, 21+16+11+10+8+1, 21+16+12+8+1, 21+16+12+9+8+1, 21+16+12+10+8+1, 21+16+13+8+1, 21+16+13+9+8+1, 21+16+13+11+8+1, 21+16+13+11+9+8+1, 21+16+13+11+10+8+1, 21+16+13+12+8+1, 21+16+13+12+9+8+1, 21+16+13+12+10+8+1, 21+16+14+8+1, 21+16+14+9+8+1, 21+16+14+11+8+1, 21+16+14+11+9+8+1, 21+16+14+11+10+8+1, 21+16+14+12+8+1, 21+16+14+12+9+8+1, 21+16+14+12+10+8+1, 21+16+15+8+1, 21+16+15+9+86+1, 21+16+15+10+8+1, 21+16+15+11+8+1, 21+16+15+11+9+8+1, 21+16+15+11+10+8+1, 21+16+15+12+8+1, 21+16+15+12+9+8+1, 21+16+15+12+10+8+1, 21+17+8+1, 21+17+9+8+1, 21+17+10+8+1, 21+17+11+8+1, 21+17+11+9+8+1, 21+17+11+10+8+1, 21+17+12+8+1, 21+17+12+9+8+1, 21+17+12+10+8+1, 21+17+13+8+1, 21+17+13+9+8+1, 21+17+13+11+8+1, 21+17+13+11+9+8+1, 21+17+13+11+10+8+1, 21+17+13+12+8+1, 21+17+13+12+9+8+1, 21+17+13+12+10+8+1, 21+17+14+8+1, 21+17+14+9+8+1, 21+17+14+11+8+1, 21+17+14+11+9+8+1, 21+17+14+11+10+8+1, 21+17+14+12+8+1, 21+17+14+12+9+8+1, 21+17+14+12+10+8+1, 21+17+15+8+1, 21+17+15+9+8+1, 21+17+15+10+8+1, 21+17+15+11+8+1, 21+17+15+11+9+8+1, 21+17+15+11+10+8+1, 21+17+15+12+8+1, 21+17+15+12+9+8+1, 21+17+15+12+10+8+1, 21+18+8+1, 21+18+9+8+1, 21+18+11+8+1, 21+18+11+9+8+1, 21+18+11+10+8+1, 21+18+12+8+1, 21+18+12+9+8+1, 21+18+12+10+8+1, 21+18+13+8+1, 21+18+13+9+8+1, 21+18+13+11+8+1, 21+18+13+11+9+8+1, 21+18+13+11+10+8+1, 21+18+13+12+8+1, 21+18+13+12+9+8+1, 21+18+13+12+10+8+1, 21+18+14+8+1, 21+18+14+9+8+1, 21+18+14+11+8+1, 21+18+14+11+9+8+1, 21+18+14+11+10+8+1, 21+18+14+12+8+1, 21+18+14+12+9+8+1, 21+18+14+12+10+8+1, 21+18+15+8+1, 21+18+15+9+8+1, 21+18+15+10+8+1, 21+18+15+11+8+1, 21+18+15+11+9+8+1, 21+18+15+11+10+8+1, 21+18+15+12+8+1, 21+18+15+12+9+8+1, 21+18+15+12+10+8+1, 21+18+16+8+1, 21+18+16+9+8+1, 21+18+16+10+8+1, 21+18+16+11+8+1, 21+18+16+11+9+8+1, 21+18+16+11+10+8+1, 21+18+16+12+8+1, 21+18+16+12+9+8+1, 21+18+16+12+10+8+1, 21+18+16+13+8+1, 21+18+16+13+9+8+1, 21+18+16+13+11+8+1, 21+18+16+13+11+9+8+1, 21+18+16+13+11+10+8+1, 21+18+16+13+12+8+1, 21+18+16+13+12+9+8+1, 21+18+16+13+12+10+8+1, 21+18+16+14+8+1, 21+18+16+14+9+8+1, 21+18+16+14+11+8+1, 21+18+16+14+11+9+8+1, 21+18+16+14+11+10+8+1, 21+18+16+14+12+8+1, 21+18+16+14+12+9+8+1, 21+18+16+14+12+10+8+1, 21+18+16+15+8+1, 21+18+16+15+9+8+1, 21+18+16+15+10+8+1, 21+18+16+15+11+8+1, 21+18+16+15+11+9+8+1, 21+18+16+15+11+10+8+1, 21+18+16+15+12+8+1, 21+18+16+15+12+9+8+1, 21+18+16+15+12+10+8+1, 21+18+17+8+1, 21+18+17+9+8+1, 21+18+17+10+8+1, 21+18+17+11+8+1, 21+18+17+11+9+8+1, 21+18+17+11+10+8+1, 21+18+17+12+8+1, 21+18+17+12+9+8+1, 21+18+17+12+10+8+1, 21+18+17+13+8+1, 21+18+17+13+9+8+1, 21+18+17+13+11+8+1, 21+18+17+13+11+9+8+1, 21+18+17+13+11+10+8+1, 21+18+17+13+12+8+1, 21+18+17+13+12+9+8+1, 21+18+17+13+12+10+8+1, 21+18+17+14+8+1, 21+18+17+14+9+8+1, 21+18+17+14+11+8+1, 21+18+17+14+11+9+8+1, 21+18+17+14+11+10+8+1, 21+18+17+14+12+8+1, 21+18+17+14+12+9+8+1, 21+18+17+14+12+10+8+1, 21+18+17+15+8+1, 21+18+17+15+9+8+1, 21+18+17+15+10+8+1, 21+18+17+15+11+8+1, 21+18+17+15+11+9+8+1, 21+18+17+15+11+10+8+1, 21+18+17+15+12+8+1, 21+18+17+15+12+9+8+1, 21+18+17+15+12+10+8+1, 21+19+8+1, 21+19+9+8+1, 21+19+10+8+1, 21+19+11+8+1, 21+19+11+9+8+1, 21+19+11+10+8+1, 21+19+12+8+1, 21+19+12+9+8+1, 21+19+12+10+8+1, 21+19+13+8+1, 21+19+13+9+8+1, 21+19+13+11+8+1, 21+19+13+11+9+8+1, 21+19+13+11+10+8+1, 21+19+13+12+8+1, 21+19+13+12+9+8+1, 21+19+13+12+10+8+1, 21+19+14+8+1, 21+19+14+9+8+1, 21+19+14+11+8+1, 21+19+14+11+9+8+1, 21+19+14+11+10+8+1, 21+19+14+12+8+1, 21+19+14+12+9+8+1, 21+19+14+12+10+8+1, 21+19+15+8+1, 21+19+15+9+8+1, 21+19+15+10+8+1, 21+19+15+11+8+1, 21+19+15+11+9+8+1, 21+19+15+11+10+8+1, 21+19+15+12+8+1, 21+19+15+12+9+8+1, 21+19+15+12+10+8+1, 21+19+16+8+1, 21+19+16+9+8+1, 21+19+16+10+8+1, 21+19+16+11+8+1, 21+19+16+11+9+8+1, 21+19+16+11+10+8+1, 21+19+16+12+8+1, 21+19+16+12+9+8+1, 21+19+16+12+10+8+1, 21+19+16+13+8+1, 21+19+16+13+9+8+1, 21+19+16+13+11+8+1, 21+19+16+13+11+9+8+1, 21+19+16+13+11+10+8+1, 21+19+16+13+12+8+1, 21+19+16+13+12+9+8+1, 21+19+16+13+12+10+8+1, 21+19+16+14+8+1, 21+19+16+14+9+8+1, 21+19+16+14+11+8+1, 21+19+16+14+11+9+8+1, 21+19+16+14+11+10+8+1, 21+19+16+14+12+8+1, 21+19+16+14+12+9+8+1, 21+19+16+14+12+10+8+1, 21+19+16+15+8+1, 21+19+16+15+9+8+1, 21+19+16+15+10+8+1, 21+19+16+15+11+8+1, 21+19+16+15+11+9+8+1, 21+19+16+15+11+10+8+1, 21+19+16+15+12+8+1, 21+19+16+15+12+9+8+1, 21+19+16+15+12+10+8+1, 21+19+17+8+1, 21+19+17+9+8+1, 21+19+17+10+8+1, 21+19+17+11+8+1, 21+19+17+11+9+8+1, 21+19+17+11+10+8+1, 21+19+17+12+8+1, 21+19+17+12+9+8+1, 21+19+17+12+10+8+1, 21+19+17+13+8+1, 21+19+17+13+9+8+1, 21+19+17+13+11+8+1, 21+19+17+13+11+9+8+1, 21+19+17+13+11+10+8+1, 21+19+17+13+12+8+1, 21+19+17+13+12+9+8+1, 21+19+17+13+12+10+8+1, 21+19+17+14+8+1, 21+19+17+14+9+8+1, 21+19+17+14+11+8+1, 21+19+17+14+11+9+8+1, 21+19+17+14+11+10+8+1, 21+19+17+14+12+8+1, 21+19+17+14+12+9+8+1, 21+19+17+14+12+10+8+1, 21+19+17+15+8+1, 21+19+17+15+9+8+1, 21+19+17+15+10+8+1, 21+19+17+15+11+8+1, 21+19+17+15+11+9+8+1, 21+19+17+15+11+10+8+1, 21+19+17+15+12+8+1, 21+19+17+15+12+9+8+1, 21+19+17+15+12+10+8+1, 22+1, and 23+1;

in the list above the numbers refer to the embodiments according to their numbering provided hereinabove whereas "+" indicates the dependency from another embodiment. The different individualized embodiments are separated by commas. In other words, "4+2+1" for example refers to embodiment 4) depending on embodiment 2), depending on embodiment 1), i.e. embodiment "4+2+1" corresponds to the compounds of embodiment 1) further limited by the features of the embodiments 2) and 4).

Where the plural form is used for compounds, salts, pharmaceutical compositions, diseases or the like, this is intended to mean also a single compound, salt, pharmaceutical composition, disease or the like.

Any reference to a compound of Formula (I) as defined in any one of embodiments 1) to 24) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

The compounds of formula (I) as defined in any one of embodiments 1) to 24) and their pharmaceutically acceptable salts can be used as medicaments, e.g. in the form of pharmaceutical compositions for enteral (such especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of Formula (I) as defined in any one of embodiments 1) to 24).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned below in a patient comprising the administration to said patient of a pharmaceutically active amount of a compound of Formula (I) as defined in any one of embodiments 1) to 24) or a pharmaceutically acceptable salt thereof.

The compounds according to Formula (I) as defined in any one of embodiments 1) to 24), or pharmaceutically acceptable salts thereof, are useful for the prevention or treatment of disorders relating to a dysfunction of the CXCR3 receptor or dysfunction of ligands signalling through CXCR3.

Such disorders relating to a dysfunction of the CXCR3 receptor or its ligands are diseases or disorders where a modulator of a human CXCR3 receptor is required. The above mentioned disorders may in particular be defined as comprising autoimmune disorders, inflammatory diseases, infectious diseases, transplant rejection, fibrosis, neurodegenerative disorders and cancer.

Autoimmune disorders may be defined as comprising rheumatoid arthritis (RA); multiple sclerosis (MS); inflammatory bowel disease (IBD; comprising Crohn's disease and ulcerative colitis); systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis.

Inflammatory diseases may be defined as comprising asthma; COPD; atherosclerosis; myocarditis; dry eye syndrome (comprising Sjögren's dry eye syndrome); myopathies (comprising inflammatory myopathies); sarcoidosis; pulmonary arterial hypertension, especially associated with sarcoidosis; and obesity.

Infectious diseases may be defined as comprising diseases mediated by various infectious agents and complications resulting threrefrom; such as malaria, cerebral malaria, leprosy, tuberculosis, influenza, *toxoplasma gondii*, dengue, hepatitis B and C, herpes simplex, *leishmania, chlamydia trachomatis*, lyme disease, west nile virus.

Transplant rejection may be defined as comprising rejection of transplanted organs such as kidney, liver, heart, lung, pancreas, cornea, and skin; graft-versus-host diseases; and chronic allograft vasculopathy.

Fibrosis may be defined as comprising liver cirrhosis (comprising primary biliary cirrhosis (PBC) and autoimmune hepatitis), idiopathic pulmonary fibrosis, renal fibrosis, endomyocardial fibrosis, systemic sclerosis, and arthrofibrosis.

Neurodegenerative disorders may be defined as comprising neurodegeneration and conditions involving neuronal death such as multiple sclerosis (including relapsing remitting multiple sclerosis and progressive multiple sclerosis), Alzheimer's disease, Parkinson's disease, Huntington's chorea, HIV associated dementia, prion mediated neurodegeneration, epilepsy, stroke, cerebral ischemia, cerebral palsy, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, narcolepsy, glossopharyngeal neuralgia, mild cognitive decline, cognitive decline, spinal muscular atrophy, and cerebral malaria.

Cancer may be defined as comprising all sorts of cancers such as large intestine cancer, rectal cancer, breast cancer, lung cancer, non-small cell lung cancer, prostate cancer, esophagal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, basophil adenoma, prolactinoma, hyperprolactinemia, adenomas, endometrial cancer, colon cancer; chronic lymphocytic leukemia (CLL); and especially the metastatic spread of those cancers.

Especially, compounds of Formula (I) according to any one of embodiments 1) to 24), or pharmaceutically acceptable salts thereof, are suitable for the prevention or treatment of diseases selected from one, several or all of the following groups of diseases and disorders:

1) Autoimmune disorders selected from rheumatoid arthritis (RA); multiple sclerosis (MS); inflammatory bowel disease (IBD; comprising Crohn's disease and ulcerative colitis); systemic lupus erythematosus (SLE); psoriasis; lupus nephritis; and type I diabetes;
2) Inflammatory diseases selected from COPD; dry eye syndrome (comprising Sjögren's dry eye syndrome); myopathies (comprising inflammatory myopathies); and sarcoidosis;
3) Transplant rejection selected from graft-versus-host diseases;
4) Fibrosis selected from liver cirrhosis (comprising primary biliary cirrhosis (PBC) and autoimmune hepatitis); and
5) Neurodegenerative disorders selected from Guillain-Barré syndrome.

Most preferably, compounds of Formula (I) according to any one of embodiments 1) to 24), or pharmaceutically acceptable salts thereof, are suitable for the treatment of diseases selected from rheumatoid arthritis, multiple sclerosis, neuromyelitis optica, inflammatory bowel disease, Crohn's disease, ulcerative colitis, systemic lupus erythematosus, psoriasis, psoriatic arthritis, lupus nephritis, interstitial cystitis, celiac disease, myasthenia gravis, type I diabetes, uveitis, asthma, chronic obstructive pulmonary disorder, atherosclerosis, myocarditis, inflammatory myopathies, dry eye disease, sarcoidosis, influenza, cerebral malaria, transplant rejection, liver cirrhosis, systemic sclerosis, pulmonary arterial hypertension, neurodegeneration, Alzheimer's disease, HIV associated dementia, Huntington's chorea, Guillain-Barré syndrome, chronic inflammatory demyelinating polyneuropathy, brain tumor, colon cancer, breast cancer, or metastatic spread of cancer.

Preparation of Compounds of Formula (I)

A further aspect of the invention is a process for the preparation of compounds of Formula (I). Compounds according to Formula (I) of the present invention can be prepared from commercially available or well known starting materials according to the methods described in the experimental part; by analogous methods; or according to the general sequence of reactions outlined below, wherein n, X, $R^1$ and $R^2$ are as defined for Formula (I). Other abbreviations used herein are explicitly defined, or are as defined in the experimental section. In some instances the generic groups $R^1$ and $R^2$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

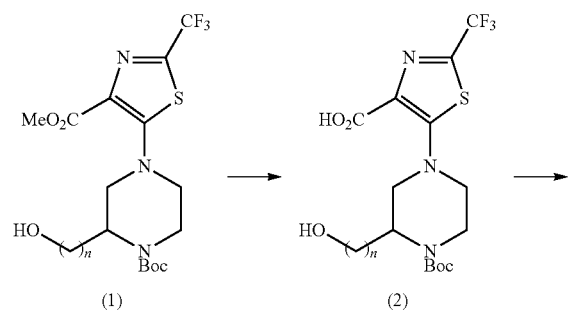

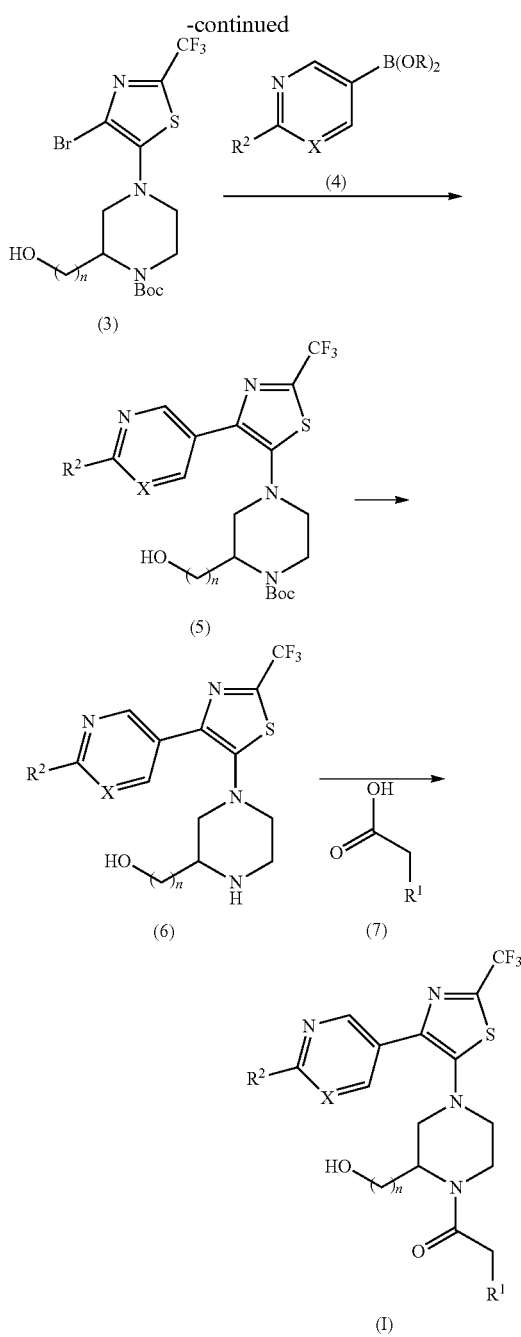

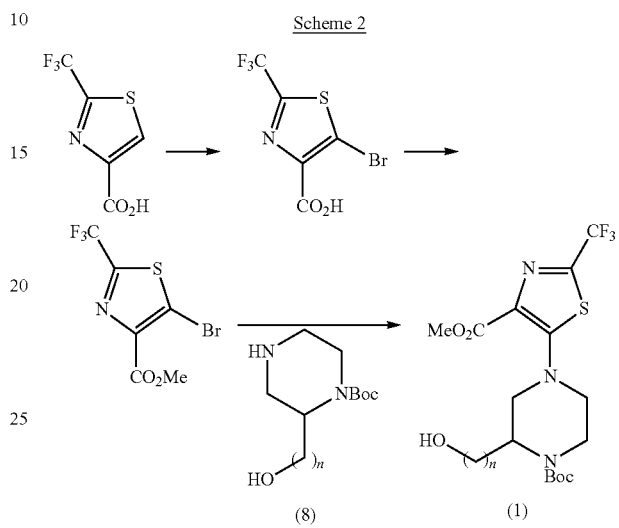

dioxane and at a temperature about RT to give the compound of structure (6). Compounds of Formula (I) can be obtained in a final step by an amide coupling with a carboxylic acid derivative (7) using standard peptide coupling methods such as HATU, in presence of a suitable base such as DIPEA or $NEt_3$ and in a suitable solvent such as DCM or DMF, preferably at a temperature about RT.

Compounds of structure (1) can be synthesized following the reaction sequence outlined in Scheme 2. Commercially available 2-(trifluoromethyl)thiazole-4-carboxylic acid is treated with n-butyl lithium and bromine in THF at a temperature around −78° C. The resulting brominated compound can be esterified using concentrated sulphuric acid in MeOH and heating at a temperature around 70° C. Nucleophilic aromatic substitution using commercially available piperazine derivatives (8), in presence of a suitable base such as DIPEA, in a suitable solvent such as MeCN, and at a temperature around 80° C. provides compounds of structure (1).

The compounds of formula (7) are either commercially available, or can be synthesized following the route shown in Scheme 3.

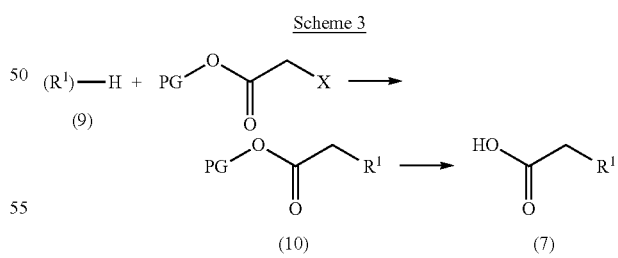

Compounds of Formula (I) can be prepared starting from intermediate (1), which is saponified under standard conditions (e.g. aq. NaOH in MeOH) to give compounds of structure (2) (Scheme 1). The carboxylic acid group in the compound of structure (2) is converted to the corresponding bromine (3) using (diacetoxyiodo)benzene and LiBr in THF at RT. Suzuki coupling can be performed using a coupling partner of structure (4), wherein R represents hydrogen or $(C_{1-4})$alkyl, using standard conditions for a Suzuki reaction, like using a suitable base such as aq. $Na_2CO_3$, a suitable palladium catalyst such as $Pd(PPh_3)_2Cl_2$, and a suitable solvent such as MeCN preferably at a temperature around 80° C. The Boc protecting group of the obtained intermediate (5) can be subsequently cleaved under acidic conditions, preferably using HCl in a suitable solvent such as A compound of structure (9) can be alkylated using an acetic acid derivative of formula X—$CH_2$—COO(PG), wherein X is a leaving group such as bromine and PG is a protecting group suitable for an acid function (e.g. benzyl), in presence of a base such as $Cs_2CO_3$ or NaH, in a suitable solvent such as MeCN or THF, and at a temperature around RT or 0° C., respectively.

Deprotection of the intermediate (10), such as benzyl deprotection under $H_2$, using Pd/C as catalyst and EtOH as solvent at a temperature around RT, leads to the compound of structure (7). Alternatively, a tert-butyl group as protecting group PG in intermediate (10) may be removed by treatment with HCl in dioxane at a temperature around RT. Other suitable acid function protecting groups and protection and deprotection methods are well known to one skilled in the art (see notably "Protective groups in organic synthesis", Greene T. W. and Wuts P. G. M., Wiley-Interscience, 1999).

If not commercially available, a compound of structure (9) wherein $R^1$ represents a di-substituted 1H-1,2,4-triazole derivative such as for instance 3-ethyl-5-methyl-1H-[1,2,4]triazole may be prepared by condensation of an imidate (e.g. ethylacetimidate) with a carboxylic acid hydrazide (e.g. propanoic acid hydrazide).

The compounds of structure (4) are either commercially available or can be prepared in analogy to methods known to one skilled in the art such as the reaction of the respective 5-bromo-pyrimidine or 3-bromo-pyridine derivative with triisopropyl borate and n-BuLi in THF and toluene at a temperature around −78° C.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Daicel ChiralPak IC (5 μm) column. Typical conditions of chiral HPLC are an isocratic mixture of eluent A (EtOH or iPrOH, in presence or absence of an amine such as $NEt_3$ or DEA) and eluent B (hexane or MeCN), at a flow rate of 0.8 to 16 mL/min.

EXPERIMENTAL SECTION

Abbreviations (as Used Herein and in the Description Above)

aq. aqueous
Boc tert.-butyloxycarbonyl
BSA Bovine serum albumine
Bu butyl
CC column chromatography on silica gel
CHO Chinese hamster ovary
CV column volume
d day(s)
DCM dichloromethane
DEA diethylamine
DIPEA N-ethyldiisopropylamine
DMF dimethylformamide
DMSO dimethylsulfoxide
EA ethyl acetate
EDTA ethylenediaminetetraacetic acid
EGTA ethylene glycol tetraacetic acid
Et ethyl
FBS fetal bovine serum
FLIPR Fluorescent imaging plate reader
Fluo-4-AM 2-{[2-(2-{5-[bis(carboxymethyl)amino]-2-methylphenoxy}ethoxy)-4-(2,7-difluoro-6-hydroxy-3-oxo-3H-xanthen-9-yl)phenyl](carboxymethyl)amino}acetic acid
G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol
h hour(s)
HATU 2-(7-Aza-1H-benzotriazole-1-yl)-1,1,3,3-tetramethyluronium
Hep heptanes
HEPES 4-(2-hydroxyethyl)-piperazine-1-ethanesulfonic acid
HV High vacuum
HPLC high performance liquid chromatography
iPr iso-propyl
LC liquid chromatography
m multiplet
M molarity [mol $L^{-1}$]
Me methyl
MS mass spectrometry
min minute(s)
NMR nuclear magnetic resonance spectroscopy
org. organic
PBS Phosphate buffered saline
Pd/C palladium on carbon
PG protecting group
Ph phenyl
Prep preparative
rpm rotations per minute
RT room temperature
s singulet
sat. Saturated
sec second(s)
TFA trifluoroacetic acid
THF tetrahydrofuran
TLC Thin layer chromatography
$t_R$ retention time
UPLC Ultra performance liquid chromatography I. Chemistry The following examples illustrate the preparation of biologically active compounds of the invention but do not at all limit the scope thereof.

General: All temperatures are stated in degrees Celsius (° C.). Unless otherwise indicated, the reactions take place at RT under an argon atmosphere and are run in a flame dried round-bottomed flask equipped with a magnetic stir bar.

Characterization Methods Used:

The LC-MS retention times have been obtained using the following elution conditions:

I) LC-MS (A):

Zorbax SB-Aq, 3.5 μm, 4.6×50 mm column thermostated at 40° C. The two elution solvents were as follows: solvent A=water+0.04% TFA; solvent B=MeCN. The eluent flow rate was 4.5 mL/min and the characteristics of the eluting mixture proportion in function of the time t from start of the elution are summarized in the table below (a linear gradient being used between two consecutive time points):

| t (min)       | 0  | 1.0 | 1.45 | 1.55 |
|---------------|----|-----|------|------|
| Solvent A (%) | 95 | 5   | 5    | 95   |
| Solvent B (%) | 5  | 95  | 95   | 5    |

II) LC-MS (B):

Acquity UPLC HSS T3 C18 1.8 μm 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1 mL/min and the characteristics of the eluting mixture proportion in function of the time t from start of the elution are summarized in the table below (a linear gradient being used between two consecutive time points):

| t (min)       | 0  | 1.4 | 1.8 | 1.9 | 2.0 |
|---------------|----|-----|-----|-----|-----|
| Solvent A (%) | 98 | 5   | 2   | 2   | 98  |
| Solvent B (%) | 2  | 95  | 98  | 98  | 2   |

III) LC-MS (C):

Acquity UPLC CSH C18 1.7 m 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1 mL/min and the characteristics of the eluting mixture proportion in function of the time t from start of the elution are summarized in the table below (a linear gradient being used between two consecutive time points):

| t (min)       | 0  | 1.4 | 1.8 | 1.9 | 2.0 |
|---------------|----|-----|-----|-----|-----|
| Solvent A (%) | 98 | 5   | 2   | 2   | 98  |
| Solvent B (%) | 2  | 95  | 98  | 98  | 2   |

Compound purity and identity was further confirmed by NMR spectroscopy (Bruker Avance II 400 MHz Ultrashield™ or Bruker Ascend™ 500 equipped with a 5 mm DCH cryoprobe), 1H (400 MHz or 500 MHz), 19F (376 MHz). The chemical shifts are reported in parts per million (ppm) relative to tetramethylsilane (TMS) or trichlorofluoromethane, and multiplicities are given as s (singlet) or m (multiplet).

Preparative LC-MS Methods Used:

The purifications by preparative LC-MS have been performed using the conditions described hereafter.

I) Preparative LC-MS (I):

A X-Bridge column (Waters C18, 10 μm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 80 | 80   | 5   | 5   | 80  | 80  |
| Solvent B (%) | 20 | 20   | 95  | 95  | 20  | 20  |

II) Preparative LC-MS (II):

A X-Bridge column (Waters C18, 10 μm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 90 | 90   | 5   | 5   | 90  | 90  |
| Solvent B (%) | 10 | 10   | 95  | 95  | 10  | 10  |

III) Preparative LC-MS (III):

An Atlantis column (Waters T3, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 3.5 | 6.0 | 6.2 | 6.6 |
|---------------|----|------|-----|-----|-----|-----|
| Solvent A (%) | 70 | 70   | 5   | 5   | 70  | 70  |
| Solvent B (%) | 30 | 30   | 95  | 95  | 30  | 30  |

IV) Preparative LC-MS (IV):

An Atlantis column (Waters T3, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 80 | 80   | 5   | 5   | 80  | 80  |
| Solvent B (%) | 20 | 20   | 95  | 95  | 20  | 20  |

V) Preparative LC-MS (V):

X-Bridge column (Waters C18, 10 μm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 3.5 | 6.0 | 6.2 | 6.6 |
|---------------|----|------|-----|-----|-----|-----|
| Solvent A (%) | 70 | 70   | 5   | 5   | 70  | 70  |
| Solvent B (%) | 30 | 30   | 95  | 95  | 30  | 30  |

VI) Preparative LC-MS (VI):

An Atlantis column (Waters T3, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 3  | 4.0 | 6.0 | 6.2 | 6.6 |
|---------------|----|------|----|-----|-----|-----|-----|
| Solvent A (%) | 95 | 95   | 50 | 5   | 5   | 95  | 95  |
| Solvent B (%) | 5  | 5    | 50 | 95  | 95  | 5   | 5   |

Preparative Chiral HPLC Methods Used:

The purifications by preparative chiral HPLC have been performed using the conditions described hereafter.

I) Preparative Chiral HPLC (I):

A ChiralPak IB column (5 μm, 30×250 mm) was used. The elution solvent was Hep/EtOH/DEA 50/50/0.1, run for 10 min and at a flow rate of 16 mL/min.

II) Preparative Chiral HPLC (II):

A ChiralPak IF column (5 μm, 20×250 mm) was used. The elution solvent was Hep/EtOH 50/50, run for 8.7 min and at a flow rate of 19 mL/min.

III) Preparative Chiral HPLC (III):

A (R,R) Whelk-01 column (10 μm, 50×250 mm) was used. The elution solvent was Hep/EtOH 70/30, run for 16.3 min and at a flow rate of 100 mL/min.

IV) Preparative Chiral HPLC (IV):

A ChiralPak IB column (5 μm, 30×250 mm) was used. The elution solvent was Hep/EtOH 70/30, run for 11.8 min and at a flow rate of 34 mL/min.

V) Preparative Chiral HPLC (V):

A ChiralPak IB column (5 μm, 30×250 mm) was used. The elution solvent was Hep/EtOH 50/50, run for 7.6 min and at a flow rate of 34 mL/min.

VI) Preparative Chiral HPLC (VI):

A ChiralPak IB column (5 μm, 30×250 mm) was used. The elution solvent was Hep/EtOH 60/40, run for 9 min and at a flow rate of 40 mL/min.

VII) Preparative Chiral HPLC (VII):

A ChiralPak IC column (5 μm, 30×250 mm) was used. The elution solvent was Hep/EtOH 70/30, run for 12 min and at a flow rate of 34 mL/min.

Example 1: 2-(3-tert-Butyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone 1.1.
5-Bromo-2-trifluoromethyl-thiazole-4-carboxylic Acid To a solution of 2-(trifluoromethyl)thiazole-4-carboxylic acid (3.2 g) in anhydrous THF (60 mL) under argon cooled down to −78° C. was added n-BuLi (1.6M in hexane, 21.3 mL) dropwise over 15 min so that the internal temperature did not rise above −60° C. A solution of $Br_2$ (0.92 mL) in cyclohexane (8 mL) was then added dropwise to keep the internal temperature below −60° C. The resulting mixture was stirred at −78° C. for 2 h and carefully quenched by addition of water (50 mL). Citric acid (10%) was added until pH=2 and the mixture was extracted with EA. The org. layers were washed with brine, dried ($MgSO_4$), filtered off and evaporated to dryness to afford 4.15 g of brown solid, used without further purification. LC-MS (A): $t_R$=0.67 min. F-NMR ($CD_3OD$): −63.57 ppm (s).

1.2.
5-Bromo-2-trifluoromethyl-thiazole-4-carboxylic Acid Methyl Ester

To a solution of intermediate 1.1 (12 g), MeOH (130 mL) was added $H_2SO_4$ (96%, 6.5 mL) and the mixture stirred at 70° C. for 3 h. After cooling down, the reaction mixture was quenched with sat. aq. $Na_2CO_3$ and the solvent partially evaporated off. The residue was diluted with DCM and washed with aq. sat. $Na_2CO_3$ (1×), water (1×) and brine (1×), and the aq. phases were extracted with DCM (2×). The combined org. layers were dried over $MgSO_4$, filtrated off, evaporated and dried under HV to afford 12 g of brown resin. LC-MS (A): $t_R$=0.83 min. F-NMR ($CD_3OD$): −63.59 ppm (s).

1.3. (S)-2-Hydroxymethyl-4-(4-methoxycarbonyl-2-trifluoromethyl-thiazol-5-yl)-piperazine-1-carboxylic Acid tert-butyl Ester To a solution of intermediate 1.2 (4 g) in MeCN (100 mL) were added (S)-1-Boc-2-hydroxymethylpiperazine (3.07 g) and DIPEA (3.54 mL) at RT. The reaction mixture was stirred at 80° C. for 28 h. After cooling down, the reaction mixture was diluted with EA and washed with water (2×) and brine. The aq. layers were extracted with EA. The combined org. layers were dried over $MgSO_4$, filtrated off and evaporated to dryness. The crude was purified by CC (Biotage, SNAP 340 g, solvent A: Hep; solvent B: EA; gradient in % B: 30 over 3CV, 30 to 50 over 5CV, 50 over 3CV) to afford 4 g of yellow foam. LC-MS (A): $t_R$=0.87 min; [M+H]⁺: 426.0.

1.4. (S)-4-(4-Carboxy-2-trifluoromethyl-thiazol-5-yl)-2-hydroxymethyl-piperazine-1-carboxylic Acid tert-butyl Ester To a solution of intermediate 1.3 (3.96 g) in EtOH (20 mL) was added 1M NaOH (20 mL) at RT and the reaction mixture was stirred for 1 h 10. The solvent was evaporated off and the residue acidified to pH 2-3 by the addition of aq. citric acid (10%). The aq. layer was extracted with DCM (3×) and the combined org. layers were dried over $MgSO_4$ and concentrated to dryness to afford 2.89 g as beige solid. LC-MS (A): $t_R$=0.79 min; [M+H]⁺: 412.1.

1.5. (S)-4-(4-Bromo-2-trifluoromethyl-thiazol-5-yl)-2-hydroxymethyl-piperazine-1-carboxylic Acid tert-butyl Ester To a solution of intermediate 1.4 (2.88 g) in THF (55 mL) were added LiBr (614 mg) and (diacetoxyiodo)benzene (2.3 g) at RT. The resulting suspension was stirred at RT overnight. The reaction mixture was evaporated off and the residue taken up with $H_2O$/DCM and extracted with DCM (3×). The combined org. layers were dried over $MgSO_4$, filtrated off and evaporated to dryness. The crude was purified by CC (Biotage, SNAP 100 g cartridge, solvent A: Hep; solvent B: EA; gradient in % B: 10 for 5CV, 10 to 30 over 5CV, 40 for 3CV) to afford 2.5 g as white solid. LC-MS (A): $t_R$=0.93 min; [M+H]⁺: 445.9.

1.6. (S)-2-Hydroxymethyl-4-[2-trifluoromethyl-4-(2-trifluoromethyl-pyrimidin-5-yl)-thiazol-5-yl]-piperazine-1-carboxylic Acid tert-butyl Ester A mixture of intermediate 1.5 (2.3 g), 2-(trifluoromethyl) pyrimidine-5-boronic acid (1.65 g), Pd(PPh₃)₂Cl₂ (202 mg), 1M $Na_2CO_3$ (15 mL) in MeCN (15 mL) was vigorously stirred at 80° C. under argon for 20 h. The reaction mixture was allowed to cool down to RT, diluted with $H_2O$ and extracted with DCM (3×). The combined org. layers were dried over $MgSO_4$, filtrated off and evaporated to dryness. The crude was purified by CC (Biotage, SNAP 340 g cartridge, solvent A: Hep; solvent B: EA; gradient in % B: 10 for 5CV, 10 to 30 over 6CV, 30 for 3CV) to afford 2.22 g as yellow foam. LC-MS (A): $t_R$=0.98 min; [M+H]⁺: 513.9.

1.7. {(S)-4-[2-Trifluoromethyl-4-(2-trifluoromethyl-pyrimidin-5-yl)-thiazol-5-yl]-piperazin-2-yl}-methanol; as Hydrochloride Salt A mixture of intermediate 1.6 (2.25 g) in HCl (22 mL, 4M in dioxane) was stirred at RT for 1 h. The reaction mixture was evaporated and dried under HV to give 2.18 g as brown foam. LC-MS (A): $t_R$=0.67 min; [M+H⁺+CH₃CN]⁺: 413.2.

1.8. (3-tert-Butyl-[1,2,4]triazol-1-yl)-acetic Acid Benzyl Ester

To a solution of 3-tert-butyl-1H-1,2,4-triazole (225 mg) in MeCN (12 mL) was added $Cs_2CO_3$ (586 mg) followed by benzyl bromoacetate (0.29 mL) and the mixture was stirred at RT for 1 h 45. The reaction mixture was diluted with EA and washed with water (2×) and brine. The aq. layers were extracted with EA (2×) and the combined org. layers were dried over $MgSO_4$, filtered off and evaporated to dryness. The residue was purified by CC (Biotage, SNAP 25 g cartridge, solvent A: DCM; solvent B: DCM/MeOH 8:2; gradient in % B: 15 for 8CV) to afford 216 mg as yellowish solid (single regioisomer). LC-MS (A): $t_R$=0.73 min; $[M+H]^+$: 274.1.

1.9. (3-tert-Butyl-[1,2,4]triazol-1-yl)-acetic Acid

A flask containing intermediate 1.8 (202 mg), Pd/C (39 mg) in EtOH (2 mL) was evacuated and backfilled with argon (3×), afterwards evacuated and backfilled with $H_2$ (3×) and the reaction mixture stirred at RT for 2 h. The reaction mixture was filtered over a celite plug and the filtrate was evaporated to dryness to afford 130 mg as white solid. LC-MS (A): $t_R$=0.36 min; $[M+H]^+$: 184.3.

1.10. 2-(3-tert-Butyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone A mixture of intermediate 1.7 (30 mg), intermediate 1.9 (11 mg), HATU (26 mg), and $NEt_3$ (26 µL) in DCM (1.5 mL) was stirred at RT overnight. The reaction mixture was evaporated to dryness and the crude was purified by Prep LC-MS (IV) to afford 6 mg as white solid. LC-MS (C): $t_R$=1.12 min; $[M+H]^+$: 579.2.

Example 2: 2-(3,5-Dimethyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone To a solution of intermediate 1.7 (2.15 g) in DCM (66 mL) were added (3,5-dimethyl-1H-1,2,4-triazole-1-yl)acetic acid (743 mg), DIPEA (2.05 mL) and HATU (2.37 g) at RT and the mixture was stirred at RT for 3 h. The reaction mixture was diluted with DCM and washed with 1M $NaHSO_4$, aq. sat. $NaHCO_3$ and brine. The aq. layers were re-extracted with 2×DCM and the combined org. layers were dried over $MgSO_4$, filtrated off and evaporated to dryness. Purification by CC (Biotage, SNAP 100 g cartridge, solvent A: DCM; solvent B: DCM/MeOH 8:2+0.1% $Et_3N$; gradient in % B: 15 for 5CV, 15 to 25 over 3CV, 25 for 5CV). Residual DIPEA in the product was removed by extraction in $DCM/H_2O$ to give 778 mg as white solid.
LC-MS (C): $t_R$=0.97 min; $[M+H]^+$: 551.1.

Example 3: 2-(3-Cyclopropyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone

3.1. (3-Cyclopropyl-[1,2,4]triazol-1-yl)-acetic Acid Benzyl Ester

To a solution of 3-cyclopropyl-1H-1,2,4-triazole (500 mg) in THF (10 mL) was added NaH (60% in oil, 174 mg) at 0° C. and the mixture was stirred for 5 min. Benzyl bromoacetate (0.719 mL) was then added and the reaction mixture was stirred for 45 min at 0° C. The mixture was quenched with sat. aq. $NH_4Cl$ and the aq. layer was extracted with EA (3×). The combined org. layers were dried over $MgSO_4$, filtrated off and evaporated to dryness. Purification by CC (Biotage, SNAP 25 g cartridge, solvent A: DCM; solvent B: MeOH; gradient in % B: 1 for 4CV, 1 to 10 over 10 CV, 10 for 2CV) afforded 831 mg as a mixture of regioisomers. Separation by preparative chiral HPLC (II) afforded two regioisomers:

First eluting fraction: (5-cyclopropyl-[1,2,4]triazol-1-yl)-acetic acid benzyl ester. LC-MS (A): $t_R$=0.75 min; $[M+H]^+$: 258.1. Roesy signal seen between $CH_2CO_2$ at 5.04 ppm and CH (cyclopropyl) at 1.74 ppm.

Second eluting fraction: (3-cyclopropyl-[1,2,4]triazol-1-yl)-acetic acid benzyl ester. LC-MS (A): $t_R$=0.75 min; $[M+H]^+$: 258.1. Roesy signal seen between $CH_2CO_2$ at 4.94 ppm and CH (triazole) at 8.08 ppm.

3.2. (3-Cyclopropyl-[1,2,4]triazol-1-yl)-acetic Acid

This compound was prepared using a method analogous to that of Example 1, step 1.9, intermediate 3.1 ((3-cyclopropyl-[1,2,4]triazol-1-yl)-acetic acid benzyl ester) replacing intermediate 1.8. LC-MS (A): $t_R$=0.33 min; $[M+H]^+$: 168.47.

3.3. 2-(3-Cyclopropyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 1, step 1.10, intermediate 3.2 replacing intermediate 1.9. The crude was purified by Prep LC-MS (IV). LC-MS (C): $t_R$=1.05 min; $[M+H]^+$: 563.1.

Example 4: 1-{(S)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone

4.1. (3-Isopropyl-[1,2,4]triazol-1-yl)-acetic Acid Benzyl Ester

This compound was prepared using a method analogous to that of Example 1, step 1.8, 3-isopropyl-1H-1,2,4-triazole replacing 3-tert-butyl-1H-1,2,4-triazole. The mixture of regioisomers was purified by preparative chiral HPLC (III). First eluting fraction: (3-isopropyl-[1,2,4]triazol-1-yl)-acetic acid benzyl ester. LC-MS (A): $t_R$=0.76 min; $[M+H]^+$: 260.2. Roesy signal seen between $CH_2$ at 4.96 ppm and CH (triazole) at 8.08 ppm.

Second eluting fraction: (5-isopropyl-[1,2,4]triazol-1-yl)-acetic acid benzyl ester. LC-MS (A): $t_R$=0.76 min; $[M+H]^+$: 260.2. Roesy signal seen between $CH_2$ at 4.96 ppm and CH (isopropyl) at 2.97 ppm.

4.2. (3-Isopropyl-[1,2,4]triazol-1-yl)-acetic Acid

This compound was prepared using a method analogous to that of Example 1, step 1.9, (3-isopropyl-[1,2,4]triazol-1-yl)-acetic acid benzyl ester from step 4.1 replacing intermediate 1.8. LC-MS (A): $t_R$=0.30 min; $[M+H]^+$: 170.2.

4.3. 1-{(S)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone This compound was prepared using a method analogous to that of Example 1, step 1.10, intermediate 4.2 replacing intermediate 1.9. The crude was purified by Prep LC-MS (IV). LC-MS (C): $t_R$=1.07 min; [M+H]$^+$: 564.9.

Example 5: 1-{(S)-2-Hydroxymethyl-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone 5.1. (3-Trifluoromethyl-[1,2,4]triazol-1-yl)-acetic Acid Benzyl Ester This compound was prepared using a method analogous to that of Example 1, step 1.8, 3-(trifluoromethyl)-1H-1,2,4-triazole replacing 3-tert-butyl-1H-1,2,4-triazole. The desired compound was obtained after CC as single regioisomer. LC-MS (A): $t_R$=0.85 min; [M+H]$^+$: 286.1.

5.2. (3-Trifluoromethyl-[1,2,4]triazol-1-yl)-acetic Acid

This compound was prepared using a method analogous to that of Example 1, step 1.9, intermediate 5.1 replacing intermediate 1.8. LC-MS (A): $t_R$=0.42 min; [M+H]$^+$: 196.1.

5.3. 1-{(S)-2-Hydroxymethyl-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone This compound was prepared using a method analogous to that of Example 1, step 1.10, intermediate 5.2 replacing intermediate 1.9. Additional 1.1 eq of HATU and 1 eq of intermediate 5.2 were added and the reaction mixture was further stirred for 24 h. The crude was purified by Prep LC-MS (IV). LC-MS (C): $t_R$=1.15 min; [M+H]$^+$: 591.1.

Example 6: 1-{(S)-4-[4-(2-Ethoxy-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone 6.1. (S)-4-[4-(2-Ethoxy-pyrimidin-5-yl)-2-trifluoromethyl-thiazol-5-yl]-2-hydroxymethyl-piperazine-1-carboxylic Acid tert-butyl Ester This compound was prepared using a method analogous to that of Example 1, step 1.6, 2-ethoxypyrimidine-5-boronic acid replacing 2-(trifluoromethyl)pyrimidine-5-boronic acid. LC-MS (A): $t_R$=0.92 min; [M+H]$^+$: 490.2.

6.2. (S)-(4-(4-(2-Ethoxypyrimidin-5-yl)-2-(trifluoromethyl) thiazol-5-yl)piperazin-2-yl)methanol, as Hydrochloride Salt This compound was prepared using a method analogous to that of Example 1, step 1.7, intermediate 6.1 replacing intermediate 1.6. LC-MS (A): $t_R$=0.57 min; [M+H]$^+$: 390.2.

6.3. 1-{(S)-4-[4-(2-Ethoxy-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone This compound was prepared using a method analogous to that of Example 1, step 1.10, intermediate 6.2 replacing intermediate 1.7, intermediate 5.2 replacing intermediate 1.9 and DMF replacing DCM. The crude was purified by Prep LC-MS (I). LC-MS (C): $t_R$=1.09 min; [M+H]$^+$: 567.1.

Example 7: 2-(3,5-Dimethyl-[1,2,4]triazol-1-yl)-1-{(S)-4-[4-(2-ethoxy-pyrimidin-5-yl)-2-trifluoromethyl-thiazol-5-yl]-2-hydroxymethyl-piperazin-1-yl}-ethanone This compound was prepared using a method analogous to that of Example 6, step 6.3, 3,5-dimethyl-1H-1,2,4-triazol-1-yl)acetic acid replacing intermediate 5.2. The crude was purified by Prep LC-MS (I). LC-MS (B): $t_R$=1.28 min; [M+H]$^+$: 527.2.

Example 8: 1-{(S)-4-[4-(2-Cyclopropyl-pyrimidin-5-yl)-2-trifluoromethyl-thiazol-5-yl]-2-hydroxymethyl-piperazin-1-yl}-2-(3,5-di methyl-[1,2,4]triazol-1-yl)-ethanone 8.1. (S)-4-[4-(2-Cyclopropyl-pyrimidin-5-yl)-2-trifluoromethyl-thiazol-5-yl]-2-hydroxymethyl-piperazine-1-carboxylic Acid tert-butyl Ester This compound was prepared using a method analogous to that of Example 1, step 1.6, 2-cyclopropyl-5-(4,4,5,5-tetramethyl-1,3,2-dioxaborolan-2-yl)pyrimidin replacing 2-(trifluoromethyl)pyrimidine-5-boronic acid. LC-MS (A): $t_R$=0.92 min; [M+H]$^+$: 486.2.

8.2. (S)-(4-(4-(2-Cyclopropylpyrimidin-5-yl)-2-(trifluoromethyl)thiazol-5-yl)piperazin-2-yl)methanol, as Hydrochloride Salt This compound was prepared using a method analogous to that of Example 1, step 1.7, intermediate 8.1 replacing intermediate 1.6. LC-MS (A): $t_R$=0.57 min; [M+H]$^+$: 386.1.

8.3. 1-{(S)-4-[4-(2-Cyclopropyl-pyrimidin-5-yl)-2-trifluoromethyl-thiazol-5-yl]-2-hydroxymethyl-piperazin-1-yl}-2-(3, 5-dimethyl-[1,2,4]triazol-1-yl)-ethanone This compound was prepared using a method analogous to that of Example 7, intermediate 8.2 replacing intermediate 6.2. The crude was purified by Prep LC-MS (I). LC-MS (C): $t_R$=0.9 min; [M+H]$^+$: 523.2.

Example 9: 1-{(S)-4-[4-(2-Cyclopropyl-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone This compound was prepared using a method analogous to that of Example 8, step 8.3, intermediate 5.2 replacing (3,5-dimethyl-1H-1,2,4-triazol-1-yl)acetic acid. The crude was purified by Prep LC-MS (I) followed by Prep TLC (DCM/MeOH 97:3). LC-MS (C): $t_R$=1.1 min; [M+H]$^+$: 563.1.

Example 10: 1-{(R)-2-Hydroxymethyl-4-[2-trifluoromethyl-4-(6-trifluoromethyl-pyridin-3-yl)-thiazol-5-yl]-piperazin-1-yl}-2-(3-isopropyl-[1,2,4]triazol-1-yl)-ethanone 10.1. (R)-4-(4-Bromo-2-trifluoromethyl-thiazol-5-yl)-2-hydroxymethyl-piperazine-1-carboxylic Acid tert-butyl Ester This compound was prepared using a method analogous to that of Example 1, following steps 1.1 to steps 1.5, (R)-1-Boc-2-hydroxymethylpiperazine replacing (S)-1-Boc-2-hydroxymethylpiperazine in step 1.3. LC-MS (A): $t_R$=0.92 min; [M+H]$^+$: 445.9.

10.2. (R)-2-Hydroxymethyl-4-[2-trifluoromethyl-4-(6-trifluoromethyl-pyridin-3-yl)-thiazol-5-yl]-piperazine-1-carboxylic Acid tert-butyl Ester This compound was prepared using a method analogous to that of Example 1, step 1.6, 2-(trifluoromethyl)pyridine-5-boronic acid replacing 2-(trifluoromethyl)pyrimidine-5-boronic acid. LC-MS (A): $t_R$=0.99 min; [M+H]$^+$: 512.9.

10.3. (R)-(4-(2-(trifluoromethyl)-4-(6-(trifluoromethyl)pyridin-3-yl)thiazol-5-yl)piperazin-2-yl)methanol, as Hydrochloride Salt This compound was prepared using a method analogous to that of Example 1, step 1.7, intermediate 10.2 replacing intermediate 1.6. LC-MS (A): $t_R$=0.68 min; [M+H]$^+$: 413.1.

10.4. 1-{(R)-2-Hydroxymethyl-4-[2-trifluoromethyl-4-(6-trifluoromethyl-pyridin-3-yl)-thiazol-5-yl]-piperazin-1-yl}-2-(3-isopropyl-[1,2,4]triazol-1-yl)-ethanone This compound was prepared using a method analogous to that of Example 4, step 4.3, intermediate 10.3 replacing intermediate 1.7 and DMF replacing DCM. The crude was purified by Prep LC-MS (I). LC-MS (C): $t_R$=1.1 min; [M+H]$^+$: 564.2.

Example 11: 1-{(R)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone

11.1. (R)-2-Hydroxymethyl-4-[2-trifluoromethyl-4-(2-trifluoromethyl-pyrimidin-5-yl)-thiazol-5-yl]-piperazine-1-carboxylic Acid tert-butyl Ester This compound was prepared using a method analogous to that of Example 10, step 10.2, 2-(trifluoromethyl)pyrimidine-5-boronic acid replacing 2-(trifluoromethyl)pyridine-5-boronic acid. LC-MS (A): $t_R$=0.98 min; [M+H]$^+$: 513.9.

11.2. (R)-(4-(2-(trifluoromethyl)-4-(2-(trifluoromethyl)pyrimidin-5-yl)thiazol-5-yl) piperazin-2-yl)methanol, as Hydrochloride Salt This compound was prepared using a method analogous to that of Example 10, step 10.3, intermediate 11.1 replacing intermediate 10.2. LC-MS (A): $t_R$=0.67 min; [M+H]$^+$: 414.0.

11.3. 1-{(R)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone This compound was prepared using a method analogous to that of Example 10, step 10.4, intermediate 11.2 replacing intermediate 10.3. The crude was purified by Prep LC-MS (I). LC-MS (C): $t_R$=1.07 min; [M+H]$^+$: 565.4.

Example 12: 2-(3,5-Dimethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 11, step 11.3, (3,5-dimethyl-1H-1,2,4-triazol-1-yl)acetic acid replacing intermediate 4.2. The crude was purified by Prep LC-MS (II). LC-MS (C): $t_R$=0.97 min; [M+H]$^+$: 551.1.

Example 13: 2-Benzoimidazol-1-yl-1-{(R)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 11, step 11.3, 2-(1H-benzimidazol-1-yl)acetic acid replacing intermediate 4.2. The crude was purified by Prep LC-MS (I). LC-MS (C): $t_R$=0.89 min; [M+H]$^+$: 572.1.

Example 14: 2-(5-Fluoro-indol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 11, step 11.3, (5-fluoroindol-1-yl)acetic acid replacing intermediate 4.2. The crude was purified by Prep LC-MS (V). LC-MS (C): $t_R$=1.25 min; [M+H]$^+$: 589.1.

Example 15: 1-{(R)-2-Hydroxymethyl-4-[2-trifluoromethyl-4-(2-trifluoromethyl-pyrimidin-5-yl)-thiazol-5-yl]-piperazin-1-yl}-2-(5-methoxy-indol-1-yl)-ethanone This compound was prepared using a method analogous to that of Example 11, step 11.3, (5-methoxy-1H-indol-1-yl)acetic acid replacing intermediate 4.2. The crude was purified by Prep LC-MS (I). LC-MS (C): $t_R$=1.22 min; [M+H]$^+$: 601.1.

Example 16: 1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone

16.1. (3-Methyl-[1,2,4]triazol-1-yl)-acetic Acid Benzyl Ester

This compound was prepared using a method analogous to that of Example 1, step 1.8, 3-methyl-1H-1,2,4-triazole replacing 3-tert-butyl-1H-1,2,4-triazole. The mixture of regioisomers was purified by preparative chiral HPLC (IV). First eluting fraction: (5-methyl-[1,2,4]triazol-1-yl)-acetic acid benzyl ester. LC-MS (A): $t_R$=0.68 min; [M+H]$^+$: 232.16. $^1$H-NMR (CDCl$_3$): 7.83 (s, 1H); 7.40-7.33 (m, 5H); 5.23 (s, 2H); 4.93 (s, 2H); 2.43 (s, 3H). Roesy signal seen between CH$_2$ at 4.93 ppm and CH$_3$ at 2.43 ppm.
Second eluting fraction: (3-methyl-[1,2,4]triazol-1-yl)-acetic acid benzyl ester. LC-MS (A): $t_R$=0.67 min; [M+H]$^+$: 232.16. $^1$H-NMR (CDCl$_3$): 8.05 (s, 1H); 7.40-7.30 (m, 5H);

5.23 (s, 0.95H, CH₂); 4.93-4.88 (3 s, 2H); 2.42 (s, 3H). Roesy signal seen between CH (triazole) at 8.05 ppm and CH₂ at 4.93-4.88 ppm.

16.2. (3-Methyl-[1,2,4]triazol-1-yl)-acetic Acid

This compound was prepared using a method analogous to that of Example 1, step 1.9, (3-methyl-[1,2,4]triazol-1-yl)-acetic acid benzyl ester from step 16.1 replacing intermediate 1.8. LC-MS (A): $t_R$=0.18 min; [M+H]⁺: 142.22.

16.3. 1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone This compound was prepared using a method analogous to that of Example 11, step 11.3, intermediate 16.2 replacing intermediate 4.2. The crude was purified by Prep LC-MS (II). LC-MS (B): $t_R$=1.35 min; [M+H]⁺: 537.1.

Example 17: 1-{(R)-2-Hydroxymethyl-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone

17.1. (3-Methoxymethyl-[1,2,4]triazol-1-yl)-acetic Acid Benzyl Ester

This compound was prepared using a method analogous to that of Example 1, step 1.8, 3-(methoxymethyl)-1H-1,2,4-triazole replacing 3-tert-butyl-1H-1,2,4-triazole. The crude was purified by two CC (1. Biotage, SNAP 10 g cartridge, solvent A: DCM; solvent B: DCM/MeOH 8:2; gradient in % B: 5 for 7CV, 5 to 15 over 3CV, 15 for 3CV. 2. Biotage, SNAP 10 g cartridge, solvent A: DCM; solvent B: DCM/MeOH 8:2; gradient in % B: 5 for 5CV, 5 to 10 over 3CV, 10 for 3CV, 10 to 15 for 3 CV) to yield two regioisomers:

First eluting fraction: (5-methoxymethyl-[1,2,4]triazol-1-yl)-acetic acid benzyl ester: colourless oil. LC-MS (A): $t_R$=0.71 min; [M+H]⁺: 262.2.

Second eluting fraction: (3-methoxymethyl-[1,2,4]triazol-1-yl)-acetic acid benzyl ester: colourless oil. LC-MS (A): $t_R$=0.67 min; [M+H]⁺: 262.1. Roesy signal seen between CH (triazole) at 8.17 ppm and NCH₂CO₂ at 5.01 ppm.

17.2. (3-Methoxymethyl-[1,2,4]triazol-1-yl)-acetic Acid

This compound was prepared using a method analogous to that of Example 1, step 1.9, (3-methoxymethyl-[1,2,4]triazol-1-yl)-acetic acid benzyl ester from step 17.1 replacing intermediate 1.8. LC-MS (A): $t_R$=0.24 min; [M+H]⁺: 172.0.

17.3. 1-{(R)-2-Hydroxymethyl-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone This compound was prepared using a method analogous to that of Example 11, step 11.3, intermediate 17.2 replacing intermediate 4.2. The crude was purified by Prep LC-MS (II). LC-MS (B): $t_R$=1.36 min; [M+H]⁺: 567.1.

Example 18: 1-{(R)-2-Hydroxymethyl-4-[2-trifluoromethyl-4-(2-trifluoromethyl-pyrimidin-5-yl)-thiazol-5-yl]-piperazin-1-yl}-2-[3-(5-methyl-[1,2,4]oxadiazol-3-yl)-[1,2,4]triazol-1-yl]-ethanone

18.1. 5-Methyl-3-(1H-[1,2,4]triazol-3-yl)-[1,2,4]oxadiazole

To a suspension of N-hydroxy-acetamidine (803 mg) in THF (25 mL) was added NaH (60% in oil, 434 mg) at RT. The foaming suspension was stirred at 70° C. under argon for 30 min, then methyl 1H-1,2,4-triazole-3-carboxylate (725 mg) was added and the mixture was stirred at 70° C. for 2 h 40. The reaction mixture was allowed to cool to RT, quenched with sat. NH₄Cl, filtrated off, and the precipitate was washed with THF and MeOH. The filtrate was evaporated and dried at HV to give 1.85 g as beige solid. LC-MS (A): $t_R$=0.4 min; [M+H]⁺: 152.2.

18.2. [3-(5-Methyl-[1,2,4]oxadiazol-3-yl)-[1,2,4]triazol-1-yl]-acetic Acid Benzyl Ester To a suspension of intermediate 18.1 (1.84 g) in MeCN (85 mL) and DMF (5 mL) were added Cs₂CO₃ (3.97 g) and benzyl bromoacetate (4 mL) at RT and the reaction mixture was stirred at RT overnight. The reaction mixture was evaporated to dryness, diluted with EA and washed with water (2×) and brine (1×). The aq. layers were re-extracted with EA (2×). The combined org. layers were dried over MgSO₄, filtrated off, evaporated and dried at HV. CC (Biotage, SNAP 100 g cartridge, solvent A: Hep; solvent B: EA; gradient in % B: 30 for 2CV, 30 to 50 over 3CV, 50 for 3CV, 50 to 70 over 3CV) followed by Prep LC-MS (I) afforded 341 mg as white powder (contains 22 mol % of intermediate 18.3). LC-MS (A): $t_R$=0.77 min; [M+H]⁺: 300.0.

18.3. [3-(5-methyl-[1,2,4]oxadiazol-3-yl)-[1,2,4]triazol-1-yl]-acetate, as Sodium Salt To a suspension of intermediate 18.2 (335 mg) in EtOH (3 mL) was added 1M NaOH (0.88 mL) at RT and the resulting solution was stirred at RT for 1 h. The reaction mixture was evaporated and dried at HV to give 349 mg as beige solid. LC-MS (A): $t_R$=0.39 min; [M+H]⁺: 210.1.

18.4. 1-{(R)-2-Hydroxymethyl-4-[2-trifluoromethyl-4-(2-trifluoromethyl-pyrimidin-5-yl)-thiazol-5-yl]-piperazin-1-yl}-2-[3-(5-methyl-[1,2,4]oxadiazol-3-yl)-[1,2,4]triazol-1-yl]-ethanone This compound was prepared using a method analogous to that of Example 11, step 11.3, intermediate 18.3 replacing intermediate 4.2. The crude was purified by Prep LC-MS (I). LC-MS (B): $t_R$=1.41 min; [M+H]⁺: 605.1.

Example 19: 1-{(R)-2-Hydroxymethyl-4-[2-trifluoromethyl-4-(2-trifluoromethyl-pyrimidin-5-yl)-thiazol-5-yl]-piperazin-1-yl}-2-(3-phenyl-[1,2,4]triazol-1-yl)-ethanone This compound was prepared using a method analogous to that of Example 11, step 11.3, 2-(3-phenyl-1H-1,2,4-triazol-1-yl)acetic acid replacing intermediate 4.2. The crude was purified by Prep LC-MS (I). LC-MS (C): $t_R$=1.15 min; [M+H]⁺: 599.2.

Example 20: 2-(3-Acetyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone

20.1. (3-Acetyl-[1,2,4]triazol-1-yl)-acetic Acid Benzyl Ester

This compound was prepared using a method analogous to that of Example 1, step 1.8, 1-(1H-1,2,4-triazol-5-yl)ethanone replacing 3-tert-butyl-1H-1,2,4-triazole. The crude was purified by CC (Biotage, SNAP 10 g cartridge, solvent A: Hep; solvent B: EA; gradient in % B: 30 for 4CV, 30 to 70 over 4CV, 70 for 2CV, 70 to 100 over 2CV, 100 for 2CV) to give the desired triazole regioisomer as second fraction. Roesy signal seen between CH (triazole) at 8.28 ppm and $CH_2$ at 5.1 ppm.
LC-MS (A): $t_R$=0.7 min; [M+H]$^+$: 260.1.

20.2. (3-Acetyl-[1,2,4]triazol-1-yl)-acetic Acid

This compound was prepared using a method analogous to that of Example 1, step 1.9, intermediate 20.1 replacing intermediate 1.8. LC-MS (A): $t_R$=0.25 min; [M+H]$^+$: 170.0.

20.3. 2-(3-Acetyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 11, step 11.3, intermediate 20.2 replacing intermediate 4.2 and DCM replacing DMF. The crude was purified by Prep LC-MS (II) followed by Prep LC-MS (IV). LC-MS (B): $t_R$=1.38 min; [M+H]$^+$: 565.1.

Example 21: 2-[3-(1-Hydroxy-ethyl)-[1,2,4]triazol-1-yl]-1-{(R)-2-hydroxymethyl-4-[2-trifluoromethyl-4-(2-trifluoromethyl-pyrimidin-5-yl)-thiazol-5-yl]-piperazin-1-yl}-ethanone To solution of Example 20 (40 mg) in THF (0.75 mL) and EtOH (0.25 mL) was added NaBH$_4$ (1.3 mg) and the mixture was stirred at 0° C. for 1 h 10. The reaction mixture was quenched by addition of H$_2$O and extracted with DCM (3×). The combined org. layers were evaporated and dried at HV. The crude was purified by Prep LC-MS (IV) to give 25 mg as white powder. LC-MS (B): $t_R$=1.32 min; [M+H]$^+$: 567.1.

Example 22: 1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone This compound was prepared using a method analogous to that of Example 11, step 11.3, (3-methyl-1H-pyrazol-1-yl)acetic acid replacing intermediate 4.2 and DCM replacing DMF. The crude was purified by Prep LC-MS (IV). LC-MS (C): $t_R$=1.07 min; [M+H]$^+$: 536.4.

Example 23: 1-{(R)-2-Hydroxymethyl-4-[2-trifluoromethyl-4-(2-trifluoromethyl-pyrimidin-5-yl)-thiazol-5-yl]-piperazin-1-yl}-2-(3-pyridin-2-yl-[1,2,4]triazol-1-yl)-ethanone

23.1. (3-Pyridin-2-yl-[1,2,4]triazol-1-yl)-acetic Acid tert-butyl Ester

This compound was prepared using a method analogous to that of Example 1, step 1.8, 2-(1H-1,2,4-triazol-3-yl) pyridine replacing 3-tert-butyl-1H-1,2,4-triazole and tert-butyl bromoacetate replacing benzyl bromoacetate. The compound was further purified by Prep LC-MS (VI). LC-MS (A): $t_R$=0.61 min; [M+H]$^+$: 261.2.

23.2. 2-(3-(Pyridin-2-yl)-H-1,2,4-triazol-1-yl)acetic acid, as Hydrochloride Salt To a suspension of intermediate 23.1 (263 mg) dioxane (2 mL) was added HCl (4M in dioxane; 2 mL). After 1 h at RT, few drops of H$_2$O were added and the reaction mixture was stirred for 26 h. The reaction mixture was evaporated and dried at HV to give 263 mg as yellowish solid. LC-MS (A): $t_R$=0.29 min; [M+H]$^+$: 205.1.

23.3. 1-{(R)-2-Hydroxymethyl-4-[2-trifluoromethyl-4-(2-trifluoromethyl-pyrimidin-5-yl)-thiazol-5-yl]-piperazin-1-yl}-2-(3-pyridin-2-yl-[1,2,4]triazol-1-yl)-ethanone This compound was prepared using a method analogous to that of Example 11, step 11.3, intermediate 23.2 replacing intermediate 4.2 and DCM replacing DMF. The crude was purified by Prep LC-MS (IV) followed by Prep TLC (0.5 mm, DCM/MeOH 95/5). LC-MS (C): $t_R$=1.00 min; [M+H]$^+$: 600.1.

Example 24 and Example 25: 2-(3-Ethyl-5-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone and 2-(5-Ethyl-3-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone Acid Precursors for Example 24 and 25:

Step 24.1. To ethylacetimidate hydrochloride (500 mg) in MeCN (6 mL) was added Amberlyst A21 (1.14 g) and the suspension stirred at RT for 15 min. Then the mixture was filtrated and the resin washed with MeCN (1 mL). Propanoic acid hydrazide (353 mg) was added to the filtrate and the resulting white suspension was stirred at 50° C. under argon for 4 d and at 80° C. overnight. The reaction mixture was evaporated. Purification by CC (Biotage, SNAP 10 g cartridge, solvent A: DCM; solvent B: MeOH; gradient in % B: 10 for 6CV, 10 to 20 over 3CV, 20 for 6CV) followed by a second CC (Biotage, SNAP 10 g cartridge, solvent A: DCM; solvent B: DCM/MeOH 8:2; gradient in % B: 25 for 7CV, 25 to 50 over 3CV, 50 for 5CV) afforded 3-ethyl-5-methyl-1H-[1,2,4]triazole (125 mg as yellow oil). LC-MS (A): $t_R$=0.21 min; [M+H]$^+$: 112.4.

Step 24.2: A method analogous to that of Example 1 step 1.8 was followed, 3-ethyl-5-methyl-1H-[1,2,4]triazole from step 24.1 replacing 3-tert-butyl-1H-1,2,4-triazole. A mixture of regioisomers was obtained: (3-ethyl-5-methyl-[1,2,4]triazol-1-yl)-acetic acid benzyl ester and (5-ethyl-3-methyl-[1,2,4]triazol-1-yl)-acetic acid benzyl ester.

Step 24.3: A method analogous to that of Example 1 step 1.9 was followed, intermediates from step 24.2 replacing intermediate 1.8. A mixture of regioisomers (ca. 1:1) was obtained: (3-ethyl-5-methyl-[1,2,4]triazol-1-yl)-acetic acid and (5-ethyl-3-methyl-[1,2,4]triazol-1-yl)-acetic acid.

The final compounds were prepared using a method analogous to that of Example 11, step 11.3, intermediates from step 24.3 replacing intermediate 4.2 and DCM replacing DMF. The crude was purified by Prep LC-MS (IV)

followed by preparative chiral HPLC (I). Both fractions were taken up in DCM and washed with water (2×) and the aq. layers extracted with DCM (1×). The combined org. layers were dried over MgSO$_4$, filtrated off, evaporated and dried at HV.

First eluting fraction (Example 24): 2-(3-ethyl-5-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone. LC-MS (C): $t_R$=1.00 min; [M+H]$^+$: 565.1.

Second eluting fraction (Example 25): 2-(5-ethyl-3-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone. LC-MS (C): $t_R$=1.00 min; [M+H]$^+$: 565.5.

Example 26: 1-{(R)-2-Hydroxymethyl-4-[2-trifluoromethyl-4-(2-trifluoromethyl-pyrimidin-5-yl)-thiazol-5-yl]-piperazin-1-yl}-2-imidazo[4,5-b]pyridin-3-yl-ethanone 26.1. Imidazo[4, 5-b]pyridin-3-yl-acetic Acid Benzyl Ester To a solution of 4-azabenzimidazole (4.75 g) in DMF (80 mL) was added benzyl bromoacetate (6.58 mL) followed by Cs$_2$CO$_3$ (25.9 g). The resulting suspension was stirred overnight. The reaction mixture was diluted with EA and washed with water (2×) and aq. sat. NH$_4$Cl. The aq. layers were extracted with EA (2×). The combined org. layers were dried over MgSO$_4$, filtrated off and evaporated in reduced pressure. The crude was purified by CC (Biotage, SNAP 100 g cartridge, solvent A: DCM; solvent B: DCM/MeOH 8:2; gradient in % B: 0 to 5 over 3CV, 5 for 5CV, 5 to 15 over 5CV, 15 for 3CV) to afford 4.99 g of the desired compound as yellow solid. LC-MS (B): $t_R$=0.59 min; [M+H]$^+$: 267.86.

26.2. Imidazo[4, 5-b]pyridin-3-yl-acetic Acid

To a yellow suspension of intermediate 26.1 (4.99 g) in MeOH (30 mL) and acetic acid (0.3 mL) was added Pd/C (10%, 994 mg) under argon. The flask was evacuated and backfilled with argon three times, then evacuated and backfilled with hydrogen twice. The reaction mixture was stirred at RT under hydrogen for 5 h, filtrated over celite and the celite was washed with MeOH. The filtrate was evaporated to dryness to afford 2.41 g of off-white solid that was used without purification. LC-MS (B): $t_R$=0.15 min; [M+H]$^+$: 178.24.

26.3. 1-{(R)-2-Hydroxymethyl-4-[2-trifluoromethyl-4-(2-trifluoromethyl-pyrimidin-5-yl)-thiazol-5-yl]-piperazin-1-yl}-2-imidazo[4, 5-b]pyridin-3-yl-ethanone This compound was prepared using a method analogous to that of Example 11, step 11.3, intermediate 26.2 replacing intermediate 4.2 and DCM replacing DMF. The crude was purified by Prep LC-MS (IV) followed by Prep TLC (0.5 mm, DCM/MeOH 95/5). LC-MS (A): $t_R$=0.8 min; [M+H]$^+$: 573.0.

Example 27: 2-(3,5-Dimethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone 27.1. (R)-2-(4-(2-(trifluoromethyl)-4-(2-(trifluoromethyl)pyrimidin-5-yl)thiazol-5-yl)piperazin-2-yl) ethan-1-ol, as Hydrochloride Salt This compound was prepared using a method analogous to that of Example 1, following steps 1.1 to steps 1.7, (R)-1-Boc-2-hydroxyethylpiperazine replacing (S)-1-Boc-2-hydroxymethylpiperazine in step 1.3. LC-MS (A): $t_R$=0.69 min; [M+H]$^+$: 428.0.

27.2. 2-(3, 5-Dimethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 12, intermediate 27.1 replacing intermediate 11.2 and DCM replacing DMF. The crude was purified by Prep LC-MS (I) followed by Prep TLC (0.5 mm, DCM/MeOH 97/3). LC-MS (C): $t_R$=0.98 min; [M+H]$^+$: 565.2.

Example 28: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone This compound was prepared using a method analogous to that of Example 27, step 27.2, intermediate 5.2 replacing (3,5-dimethyl-1H-1,2,4-triazol-1-yl)acetic acid. The crude was purified by Prep LC-MS (V). LC-MS (C): $t_R$=1.16 min; [M+H]$^+$: 605.1.

Example 29: 2-(3-Cyclobutyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone 29.1. (3-Cyclobutyl-[1,2,4]triazol-1-yl)-acetic Acid Benzyl Ester This compound was prepared using a method analogous to that of Example 1, step 1.8, 3-cyclobutyl-1H-1,2,4-triazole replacing of 3-tert-butyl-1H-1,2,4-triazole. A further Prep LC-MS (IV) purification was performed before submitting the regioisomeric mixture for separation to preparative chiral HPLC (V).

First eluting fraction: (5-cyclobutyl-[1,2,4]triazol-1-yl)-acetic acid benzyl ester. LC-MS (A): $t_R$=0.68 min; [M+H]$^+$: 272.2.

Second eluting fraction: (3-cyclobutyl-[1,2,4]triazol-1-yl)-acetic acid benzyl ester. (LC-MS (A): $t_R$=0.7 min; [M+H]$^+$: 272.2.

29.2. (3-Cyclobutyl-[1,2,4]triazol-1-yl)-acetic Acid

This compound was prepared using a method analogous to that of Example 1, step 1.9, (3-cyclobutyl-[1,2,4]triazol-1-yl)-acetic acid benzyl ester from step 29.1 replacing intermediate 1.8. LC-MS (A): $t_R$=0.32 min; [M+H]$^+$: 182.3. Roesy signal seen between CH (triazole) at 8.40 ppm and N—CH2-COOH at 5.02 ppm.

29.3. 2-(3-Cyclobutyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 29.2 replacing (3,5-dimethyl-1H-1,2,4-triazol-1-yl)acetic acid. The crude was purified by Prep LC-MS (IV). LC-MS (C): $t_R$=1.11 min; [M+H]$^+$: 591.2.

Example 30: 2-(3-tert-Butyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 1.9 replacing (3,5-dimethyl-1H-1,2,4-triazol-1-yl)acetic acid. The crude was purified by Prep LC-MS (I). LC-MS (C): $t_R$=1.13 min; [M+H]$^+$: 593.2.

Example 31: 2-(3-Cyclopropyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 3.2 replacing (3,5-dimethyl-1H-1,2,4-triazol-1-yl)acetic acid. The crude was purified by Prep LC-MS (I). LC-MS (C): $t_R$=1.06 min; [M+H]$^+$: 577.4.

Example 32: 2-(3-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone

32.1. (3-Ethyl-[1,2,4]triazol-1-yl)-acetic Acid Benzyl Ester

This compound was prepared using a method analogous to that of Example 1, step 1.8, 3-ethyl-1H-1,2,4-triazole replacing of 3-tert-butyl-1H-1,2,4-triazole. The mixture of regioisomers was purified by preparative chiral HPLC (VI). First eluting fraction: (5-ethyl-[1,2,4]triazol-1-yl)-acetic acid benzyl ester: LC-MS (A): $t_R$=0.72 min; [M+H]$^+$: 246.2. Roesy signal seen between $CH_2CH_3$ at 2.72 ppm and $CH_2CO_2$ at 4.93 ppm.
Second eluting fraction: (3-ethyl-[1,2,4]triazol-1-yl)-acetic acid benzyl ester: LC-MS (A): $t_R$=0.71 min; [M+H]$^+$: 246.2. Roesy signal seen between CH at 8.08 ppm and $CH_2CO_2$ at 4.96 ppm.

32.2. (3-Ethyl-[1,2,4]triazol-1-yl)-acetic Acid

This compound was prepared using a method analogous to that of Example 1, step 1.9, (3-ethyl-[1,2,4]triazol-1-yl)-acetic acid benzyl ester from step 32.1 replacing intermediate 1.8. LC-MS (A): $t_R$=0.25 min; [M+H]$^+$: 156.2.

32.3. 2-(3-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 32.2 replacing (3,5-dimethyl-1H-1,2,4-triazol-1-yl)acetic acid. The crude was purified by Prep LC-MS (IV). LC-MS (C): $t_R$=1.04 min; [M+H]$^+$: 564.9.

Example 33: 2-(5-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone

33.1. (5-Ethyl-[1,2,4]triazol-1-yl)-acetic Acid

This compound was prepared using a method analogous to that of Example 1, step 1.9, (5-ethyl-[1,2,4]triazol-1-yl)-acetic acid benzyl ester from step 32.1 replacing intermediate 1.8. LC-MS (A): $t_R$=0.22 min; [M+H]$^+$: 156.1.

33.2. 2-(5-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 33.1 replacing (3,5-dimethyl-1H-1,2,4-triazol-1-yl)acetic acid. The crude was purified by Prep LC-MS (I). LC-MS (C): $t_R$=1.03 min; [M+H]$^+$: 565.2.

Example 34: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone This compound was prepared using a method analogous to that of Example 27, step 27.2, intermediate 4.2 replacing (3,5-dimethyl-1H-1,2,4-triazol-1-yl)acetic acid. The crude was purified by Prep LC-MS (IV). LC-MS (C): $t_R$=1.08 min; [M+H]$^+$: 579.2.

Example 35: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone This compound was prepared using a method analogous to that of Example 27, step 27.2, intermediate 16.2 replacing (3,5-dimethyl-1H-1,2,4-triazol-1-yl)acetic acid. The crude was purified by Prep LC-MS (II) followed by Prep LC-MS (IV). LC-MS (C): $t_R$=1.00 min; [M+H]$^+$: 551.2.

Example 36: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(5-methyl-[1,2,4]triazol-1-yl)-ethanone

36.1. (5-Methyl-[1,2,4]triazol-1-yl)-acetic Acid

This compound was prepared using a method analogous to that of Example 1, step 1.9, (5-methyl-[1,2,4]triazol-1-yl)-acetic acid benzyl ester from step 16.1 replacing intermediate 1.8. LC-MS (A): $t_R$=0.19 min; [M+H]$^+$: 142.2.

36.2. 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(5-methyl-[1,2,4]triazol-1-yl)-ethanone This compound was prepared using a method analogous to that of Example 27, step 27.2, intermediate 36.1 replacing (3,5-dimethyl-1H-1,2,4-triazol-1-yl)acetic acid. The crude was purified by Prep LC-MS (IV). LC-MS (C): $t_R$=1.00 min; [M+H]$^+$: 551.1.

Example 37: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone This compound was prepared using a method analogous to that of Example 27, step 27.2, intermediate 17.2 replacing (3,5-dimethyl-1H-1,2,4-triazol-1-yl)acetic acid. The crude was purified by Prep LC-MS (IV). LC-MS (B): $t_R$=1.37 min; [M+H]$^+$: 581.1.

Example 38: 2-(3-Difluoromethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone 38.1. (3-Difluoromethyl-[1,2,4]triazol-1-yl)-acetic Acid Benzyl Ester This compound was prepared using a method analogous to that of Example 1, step 1.8, 3-(difluoromethyl)-1H-1,2,4-triazole replacing 3-tert-butyl-1H-1,2,4-triazole. The crude was purified by CC (Biotage, SNAP 50 g cartridge, solvent A: Hep; solvent B: EA; gradient in % B: 30 for 5CV, 30 to 70 over 5CV, 70 for 3CV, 70 to 100 over 2CV, 100 for 1CV) to yield two regiosiomers:
First eluting fraction: (5-difluoromethyl-[1,2,4]triazol-1-yl)-acetic acid benzyl ester: yellow oil. LC-MS (A): $t_R$=0.78 min; [M+H]$^+$: 268.2.
Second eluting fraction: (3-difluoromethyl-[1,2,4]triazol-1-yl)-acetic acid benzyl ester: off-white solid. LC-MS (A): $t_R$=0.77 min; [M+H]$^+$: 268.1.

38.2. (3-Difluoromethyl-[1,2,4]triazol-1-yl)-acetic Acid

This compound was prepared using a method analogous to that of Example 1, step 1.9, (3-difluoromethyl-[1,2,4]triazol-1-yl)-acetic acid benzyl ester from step 38.1 replacing intermediate 1.8. LC-MS (A): $t_R$=0.26 min; [M+H]$^+$: 178.2.

38.3. 2-(3-Difluoromethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 38.2 replacing (3,5-dimethyl-1H-1,2,4-triazol-1-yl)acetic acid. The crude was purified by Prep LC-MS (IV). LC-MS (A): $t_R$=0.86 min; [M+H]$^+$: 573.0.

Example 39: 1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-pyrazol-1-yl)-ethanone This compound was prepared using a method analogous to that of Example 27, step 27.2, (3-methyl-1H-pyrazol-1-yl)acetic acid replacing (3,5-dimethyl-1H-1,2,4-triazol-1-yl)acetic acid. The crude was purified by Prep LC-MS (IV). LC-MS (C): $t_R$=1.08 min; [M+H]$^+$: 550.0.

Example 40: 2-(3-Ethyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone 40.1 (3-Ethyl-pyrazol-1-yl)-acetic Acid Benzyl Ester This compound was prepared using a method analogous to that of Example 1, step 1.8, 3-ethyl-1H-pyrazole replacing 3-tert-butyl-1H-1,2,4-triazole. The mixture of regioisomers was purified by preparative chiral HPLC (VII). First eluting fraction: (3-ethyl-pyrazol-1-yl)-acetic acid benzyl ester: LC-MS (A): $t_R$=0.82 min; [M+H]$^+$: 245.1. Roesy signal seen between pyrazol-CH at 7.37 ppm and $CH_2CO_2$ at 4.91 ppm.

40.2 (3-Ethyl-pyrazol-1-yl)-acetic Acid

This compound was prepared using a method analogous to that of Example 1, step 1.9, (3-ethyl-pyrazol-1-yl)-acetic acid benzyl ester from step 40.1 replacing intermediate 1.8. LC-MS (A): $t_R$=0.43 min; [M+H]$^+$: 155.4.

40.3. 2-(3-Ethyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, intermediate 40.2 replacing (3,5-dimethyl-1H-1,2,4-triazol-1-yl)acetic acid. The crude was purified by Prep LC-MS (I). LC-MS (C): $t_R$=1.14 min; [M+H]$^+$: 564.0.

Example 41: 2-(3-Cyclopropyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone This compound was prepared using a method analogous to that of Example 27, step 27.2, (3-cyclopropyl-1H-pyrazol-1-yl)acetic acid replacing (3,5-dimethyl-1H-1,2,4-triazol-1-yl)acetic acid. The crude was purified by Prep LC-MS (IV). LC-MS (C): $t_R$=1.15 min; [M+H]$^+$: 576.2.

Example 42: 1-{(S)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone This compound was prepared using a method analogous to that of Example 1, step 1.10, (3-methyl-1H-pyrazol-1-yl)acetic acid replacing intermediate 1.9. The crude was purified by Prep LC-MS (I). LC-MS (C): $t_R$=1.07 min; [M+H]$^+$: 536.2.

Example 43: 2-(3-Ethyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 1, step 1.10, intermediate 40.2 replacing intermediate 1.9. The crude was purified by Prep LC-MS (I). LC-MS (C): $t_R$=1.12 min; [M+H]$^+$: 550.0.

Example 44: 2-(3-Cyclopropyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone This compound was prepared using a method analogous to that of Example 1, step 1.10, (3-cyclopropyl-1H-pyrazol-1-yl)acetic acid replacing intermediate 1.9. The crude was purified by Prep LC-MS (I). LC-MS (C): $t_R$=1.13 min; [M+H]$^+$: 562.2.

II. Biological Assays

A) FLIPR Assay:

The bioactivity of compounds is tested in a fluorometric imaging plate reader (FLIPR: Molecular Devices) using engineered CHO-K1 cells expressing the human CXCR3A (GenBank: AY242128) coupled to a G protein (Galpha(16)). Cells are plated the day prior to bioassay in F12 medium supplemented with 10% FBS and G418 and hygromycin antibiotics to maintain recombinant selection. At the day of bioassay, cells are washed and dye loaded for one hour with Fluo-4-AM (Invitrogen) in Hanks Balanced Salt Solution (Invitrogen), buffered with 20 mM Hepes at pH 7.4 and sodium bicarbonate (0.038%), containing 5 mM probenecid. This buffer, but lacking the dye and containing probenecid at a concentration of 2.5 mM, is also used for washing steps (wash buffer); or lacking both dye and probenecid but supplemented with 0.1% BSA for compound dilution steps (dilution buffer). Cells are washed free of excess dye and 60 microliter of wash buffer is added. Stock solutions of test compounds are made up at a concentration of 10 mM in DMSO, and serially diluted in dilution buffer to concentrations required for inhibition dose response curves. After a 10 minute incubation period at 37° C., 10 microliters of each compound dilution are transferred from a compound plate to the plate containing the recombinant cells in the FLIPR instrument according to the manufacturer's instructions. Following basal readings, 10 microliter CXCL10 agonist at a concentration of 20 nM (from Peprotech) is added, again using the FLIPR instrument. Changes in fluorescence are monitored before and after addition of the test compounds. Emission peak values above base level after CXCL10 addition are exported after base line subtraction.

The calculated IC$_{50}$ values may fluctuate depending on the daily assay performance. Fluctuations of this kind are known to those skilled in the art. In the case where IC$_{50}$ values have been determined several times for the same compound, mean values are given. Data are shown in Table 1.

TABLE 1

| Example No | FLIPR: IC$_{50}$ (nM) |
| --- | --- |
| 1 | 6.7 |
| 2 | 6.0 |
| 3 | 3.0 |
| 4 | 1.8 |
| 5 | 4.0 |
| 6 | 4.6 |
| 7 | 3.1 |
| 8 | 10 |
| 9 | 1.3 |
| 10 | 1.1 |
| 11 | 3.4 |
| 12 | 6.9 |
| 13 | 1.2 |

TABLE 1-continued

| Example No | FLIPR: IC$_{50}$ (nM) |
| --- | --- |
| 14 | 0.7 |
| 15 | 2.3 |
| 16 | 3.9 |
| 17 | 5.9 |
| 18 | 510 |
| 19 | 42 |
| 20 | 6.4 |
| 21 | 4.3 |
| 22 | 1.6 |
| 23 | 35 |
| 24 | 7.6 |
| 25 | 3.6 |
| 26 | 3.5 |
| 27 | 5.2 |
| 28 | 1.1 |
| 29 | 5.5 |
| 30 | 4.4 |
| 31 | 4.4 |
| 32 | 2.6 |
| 33 | 27 |
| 34 | 4.5 |
| 35 | 2.9 |
| 36 | 8.0 |
| 37 | 5.7 |
| 38 | 8.6 |
| 39 | 1.0 |
| 40 | 1.6 |
| 41 | 0.45 |
| 42 | 1.0 |
| 43 | 1.2 |
| 44 | 0.38 |

B): Receptor Internalization Assay:

Stock solutions of test compounds are made up at a concentration of 10 mM in DMSO, and serially diluted in PBS containing 0.5% BSA to concentrations required for inhibition dose response curves. Diluted compounds are then mixed with an equal volume of CXCL10 (Peprotech) diluted in PBS. Anticoagulated venous human whole blood is added to the mixture, which is then incubated in a CO$_2$ incubator at 37° C. to allow for ligand mediated receptor internalization (final CXCL10 concentration is 9 nM). After 30 min, the blood is mixed with fluorescently labeled CXCR3 and CD4 specific antibodies (Becton Dickinson) and incubated on ice for 10 minutes. Samples are then mixed with BD FACS Lysing Solution (Becton Dickinson) in order to eliminate red blood cells. After washing the cells with PBS containing 0.5% BSA, the samples are then analyzed in a flow cytometer (FACS Canto II, Becton Dickinson). For data analysis using FACSDiva software (Becton Dickinson), the mean fluorescence corresponding to CXCR3 cell surface expression was determined on CD4 positive cells. The program GraphPad Prism or similar software is used to fit the data to a single site dose response curve and to calculate IC$_{50}$ values.

The calculated IC$_{50}$ values may fluctuate depending on the daily assay performance. Fluctuations of this kind are known to those skilled in the art. In the case where IC$_{50}$ values have been determined several times for the same compound, mean values are given. Data are shown in Table 2.

TABLE 2

| Example No | Internalization IC$_{50}$ (nM) |
| --- | --- |
| 1 | 415 |
| 2 | 463 |
| 3 | 191 |

TABLE 2-continued

| Example No | Internalization IC$_{50}$ (nM) |
|---|---|
| 4 | 283 |
| 5 | 328 |
| 6 | 778 |
| 7 | 2270 |
| 8 | 3200 |
| 9 | 1520 |
| 10 | 961 |
| 11 | 339 |
| 12 | 324 |
| 13 | 1050 |
| 14 | 199 |
| 15 | 1660 |
| 16 | 542 |
| 17 | 1290 |
| 18 | 6500 |
| 19 | 3310 |
| 20 | 2380 |
| 21 | 737 |
| 22 | 105 |
| 23 | 2730 |
| 24 | 355 |
| 25 | 664 |
| 26 | 74.2 |
| 27 | 235 |
| 28 | 214 |
| 29 | 157 |
| 30 | 170 |
| 31 | 73.8 |
| 32 | 93.3 |
| 33 | 652 |
| 34 | 84.8 |
| 35 | 102 |
| 36 | 451 |
| 37 | 393 |
| 38 | 258 |
| 39 | 46.3 |
| 40 | 32.7 |
| 41 | 30.2 |
| 42 | 59.7 |
| 43 | 40.3 |
| 44 | 76.0 |

C) hERG Q-Patch Assay:

Compounds are evaluated for block of the hERG K channel using CHO cells stably expressing the hERG gene (accession number U04270, bSys, Witterswil, Switzerland) and the QPatch robotic platform (Sophion, Ballerup, Denmark) in single-cell mode at room temperature. Cells are grown in culture flasks at 37° C. in 5% CO$_2$, in culture medium (Ham's F-12 Nutrient Mixture, Invitrogen 21765-029) supplemented with 9% (v/v) fetal calf serum, 0.9% Penicillin/Streptomycin (10,000 U/mL, Invitrogen 15140148), 100 μg/mL Hygromycin B (Invitrogen 10687010). When the cells are ~80% confluent (every 2-3 days), they are either split for further culture or used for electrophysiology. For further culture, cells are detached with 0.25% Trypsin EDTA solution (Invitrogen 25200-056) and a fraction of the cells (10-30%) is reseeded in culture medium. For electrophysiology, on the experimental day, cells are detached with 0.25% Trypsin EDTA solution and all cells are suspended in suspension medium (293 SFM II, Invitrogen 11686-029) supplemented with 20 mM HEPES and 0.04 mg/mL Trypsin inhibitor. Cells are kept in suspension medium at 32-35° C. in the QPatch robot until use, at which time aliquots are transferred to the extracellular solution (in mM: NaCl 150; KCl 4; CaCl$_2$ 1.2; MgCl$_2$ 1; HEPES 10; pH 7.4 with NaOH) containing 0.3% v/v DMSO and applied to the test plates. K$^+$ currents are measured with the patch-voltage-clamp technique in the whole-cell configuration with the internal solution (in mM: KCl, 140; NaCl, 10; MgCl$_2$, 1; HEPES, 10: EGTA, 5; pH=7.2 with KOH). Currents are low-pass filtered using the internal Bessel filter of the QPatch robot with a cut-off frequency of 2 kHz and are digitized at 10 kHz. K$^+$ tail currents are produced from a holding voltage of −80 mV by a 500-ms depolarization to +20 mV followed by a 500-ms repolarization to −40 mV; tail current amplitudes are measured at the end of the repolarization to −40 mV. The pulse pattern is repeated every 10 sec during the experiment, baseline K$^+$ current is measured after 3 min in extracellular solution, test-solution containing compound is then applied, and K$^+$ current in presence of compound is measured 3 minutes after application to the cells. The respective test-solution is prepared by (1) dissolving the test-compound in pure DMSO, (2) diluting this DMSO solution in extracellular solution, and (3) adding further DMSO, such that the final test-solution has a concentration of either 300 nM or 3000 nM of the test-compound and contains 0.3% v/v DMSO. Compound effects are quantified as % block by dividing the current in presence of compound by the baseline current; two or three experiments are performed for each compound and the final value represents the mean of the results of each experiment. Data are shown in Table 3.

TABLE 3

| Example No | concentration [nM] | % block | concentration [nM] | % block |
|---|---|---|---|---|
| 1 | 300 | 2 | 3000 | 12 |
| 2 | 300 | −3 | 3000 | −4 |
| 3 | 300 | 0 | 3000 | 12 |
| 4 | 300 | 4 | 3000 | 13 |
| 5 | 300 | −2 | 3000 | 7 |
| 6 | 300 | 13 | 3000 | 23 |
| 7 | 300 | 24 | 3000 | 45 |
| 8 | 300 | 19 | 3000 | 54 |
| 9 | 300 | 8 | 3000 | 24 |
| 10 | 300 | 2 | 3000 | 12 |
| 11 | 300 | 5 | 3000 | 11 |
| 12 | 300 | 1 | 3000 | 3 |
| 13 | 300 | 5 | 3000 | 17 |
| 14 | 300 | 14 | 3000 | 62 |
| 15 | 300 | 8 | 3000 | 35 |
| 16 | 300 | 1 | 3000 | 1 |
| 17 | 300 | 2 | 3000 | 6 |
| 18 | 300 | 6 | 3000 | 13 |
| 19 | 300 | 6 | 3000 | 41 |
| 20 | 300 | 2 | 3000 | 3 |
| 22 | 300 | 4 | 3000 | 15 |
| 27 | 300 | 1 | 3000 | 4 |
| 28 | 300 | 6 | 3000 | 40 |
| 29 | 300 | 4 | 3000 | 38 |
| 30 | 300 | −2 | 3000 | 25 |
| 31 | 300 | 2 | 3000 | 23 |
| 32 | 300 | 0 | 3000 | 19 |
| 33 | 300 | −5 | 3000 | 6 |
| 34 | 300 | 10 | 3000 | 34 |
| 35 | 300 | 11 | 3000 | 25 |
| 36 | 300 | 10 | 3000 | 19 |
| 37 | 300 | 4 | 3000 | 9 |
| 39 | 300 | 1 | 3000 | 32 |
| 40 | 300 | 5 | 3000 | 47 |
| 41 | 300 | 12 | 3000 | 60 |
| 42 | 300 | 2 | 3000 | 15 |
| 43 | 300 | 5 | 3000 | 25 |
| 44 | 300 | 5 | 3000 | 34 |

The invention claimed is:

1. A compound of Formula (I)

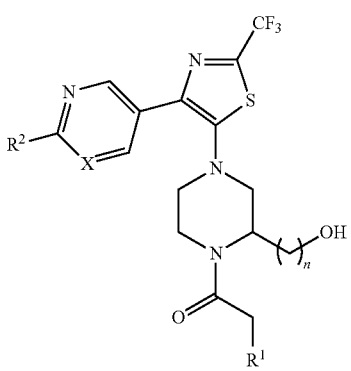

Formula (I)

wherein n represents the integer 1 or 2;

X represents N or CH;

R[1] represents heteroaryl, wherein the heteroaryl is a 5- to 10-membered monocyclic or bicyclic aromatic ring comprising 1, 2 or 3 heteroatoms independently selected from oxygen, nitrogen or sulphur, and wherein the heteroaryl is independently unsubstituted or mono- or di-substituted, wherein the substituents are independently selected from $(C_{1-4})$alkyl; $(C_{3-6})$cycloalkyl; $(C_{1-4})$alkoxy; $(C_{1-2})$alkoxy-$(C_{1-2})$alkyl; $(C_{1-2})$alkyl-carbonyl; hydroxy-$(C_{1-4})$alkyl; halogen; $(C_{1-2})$fluoroalkyl; phenyl; or heteroaryl, wherein the heteroaryl is a 5- or 6-membered monocyclic aromatic ring comprising 1, 2 or 3 heteroatoms independently selected from oxygen, nitrogen or sulphur, and wherein the heteroaryl is independently unsubstituted or mono-substituted with (C1-4)alkyl; and R[2] represents $(C_{3-6})$cycloalkyl, $(C_{1-4})$alkoxy or $(C_{1-2})$fluoroalkyl;

or a salt thereof.

2. The compound according to claim 1, wherein n represents the integer 1 or 2;

X represents N;

R[1] represents a 5-membered monocyclic heteroaryl group comprising 2 or 3 nitrogen atoms which is independently mono- or di-substituted, wherein the substituents are independently selected from $(C_{1-4})$alkyl, $(C_{3-6})$cycloalkyl, $(C_{1-2})$alkoxy-$(C_{1-2})$alkyl, hydroxy-$(C_{1-4})$alkyl or $(C_{1-2})$fluoroalkyl; or a 9-membered bicyclic aromatic ring comprising 1, 2 or 3 nitrogen atoms which is unsubstituted or mono-substituted with (C1-4)alkoxy or halogen; and R[2] represents $(C_{3-6})$cycloalkyl, $(C_{1-4})$alkoxy or trifluoromethyl;

or a salt thereof.

3. The compound according to claim 1, wherein

R[1] represents a 5-membered monocyclic heteroaryl group comprising 2 or 3 nitrogen atoms which is independently mono- or di-substituted, wherein the substituents are independently selected from $(C_{1-4})$alkyl, $(C_{3-6})$cycloalkyl or $(C_{1-2})$fluoroalkyl;

or a salt thereof.

4. The compound according to claim 1, wherein R[2] represents trifluoromethyl;

or a salt thereof.

5. The compound according to claim 1, which is also a compound of Formula ($I_{TA}$)

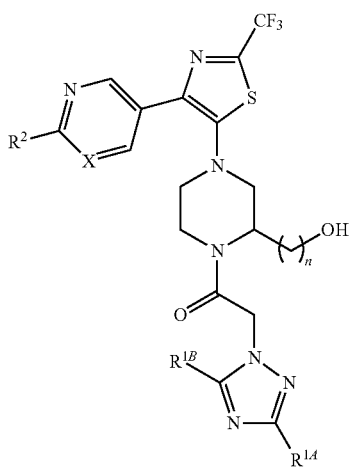

Formula ($I_{TA}$)

wherein n represents the integer 1 or 2;

R[1A] represents hydrogen, $(C_{1-4})$alkyl, $(C_{3-6})$cycloalkyl, $(C_{1-2})$alkoxy-$(C_{1-2})$alkyl, $(C_{1-2})$alkyl-carbonyl, hydroxy-$(C_{1-4})$alkyl, $(C_{1-2})$fluoroalkyl, phenyl or heteroaryl, wherein the heteroaryl is a 5- or 6-membered monocyclic aromatic ring comprising 1, 2 or 3 heteroatoms independently selected from oxygen, nitrogen or sulphur, and wherein the heteroaryl is independently unsubstituted or mono-substituted with $(C_{1-4})$alkyl;

R[1B] represents hydrogen or $(C_{1-4})$alkyl; and

R[2] represents $(C_{3-6})$cycloalkyl, $(C_{1-4})$alkoxy or $(C_{1-2})$fluoroalkyl;

or a salt thereof.

6. The compound according to claim 5, wherein

R[1A] represents $(C_{1-4})$alkyl, $(C_{3-6})$cycloalkyl, $(C_{1-2})$alkoxy-$(C_{1-2})$alkyl, hydroxy-$(C_{1-4})$alkyl or $(C_{1-2})$fluoroalkyl;

or a salt thereof.

7. The compound according to claim 5, wherein

R[1A] represents $(C_{1-4})$alkyl or $(C_{3-6})$cycloalkyl;

or a salt thereof.

8. The compound according to claim 5, wherein

R[1B] represents hydrogen;

or a salt thereof.

9. The compound according to claim 5, wherein

R[1B] represents methyl;

or a salt thereof.

10. The compound according to claim 5, wherein

R[2] represents trifluoromethyl;

or a salt thereof.

11. The compound according to claim 1, wherein the compound is:

2-(3-tert-Butyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;

2-(3,5-Dimethyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;

2-(3-Cyclopropyl-[1,2,4]triazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;

1-{(S)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;

1-{(S)-2-Hydroxymethyl-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone;

1-{(S)-4-[4-(2-Ethoxy-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone;

2-(3,5-Dimethyl-[1,2,4]triazol-1-yl)-1-{(S)-4-[4-(2-ethoxy-pyrimidin-5-yl)-2-trifluoromethyl-thiazol-5-yl]-2-hydroxymethyl-piperazin-1-yl}-ethanone;

1-{(S)-4-[4-(2-Cyclopropyl-pyrimidin-5-yl)-2-trifluoromethyl-thiazol-5-yl]-2-hydroxymethyl-piperazin-1-yl}-2-(3,5-dimethyl-[1,2,4]triazol-1-yl)-ethanone;

1-{(S)-4-[4-(2-Cyclopropyl-pyrimidin-5-yl)-2-trifluoromethyl-thiazol-5-yl]-2-hydroxymethyl-piperazin-1-yl}-2-(3-trifluoromethyl-[1,2,4]triazol-1-yl)-ethanone;

1-{(R)-2-Hydroxymethyl-4-[2-trifluoromethyl-4-(6-trifluoromethyl-pyridin-3-yl)-thiazol-5-yl]-piperazin-1-yl}-2-(3-isopropyl-[1,2,4]triazol-1-yl)-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;

2-(3,5-Dimethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

2-Benzoimidazol-1-yl-1-{(R)-2-hydroxymethyl-4-[2-trifluoromethyl-4-(2-trifluoromethyl-pyrimidin-5-yl)-thiazol-5-yl]-piperazin-1-yl}-ethanone;

2-(5-Fluoro-indol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(5-methoxy-indol-1-yl)-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-[3-(5-methyl-[1,2,4]oxadiazol-3-yl)-[1,2,4]triazol-1-yl]-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-phenyl-[1,2,4]triazol-1-yl)-ethanone;

2-(3-Acetyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

2-[3-(1-Hydroxy-ethyl)-[1,2,4]triazol-1-yl]-1-{(R)-2-hydroxymethyl-4-[2-trifluoromethyl-4-(2-trifluoromethyl-pyrimidin-5-yl)-thiazol-5-yl]-piperazin-1-yl}-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-(3-pyridin-2-yl-[1,2,4]triazol-1-yl)-ethanone;

2-(3-Ethyl-5-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

2-(5-Ethyl-3-methyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

1-{(R)-2-Hydroxymethyl-4-[2-trifluoromethyl-4-(2-trifluoromethyl-pyrimidin-5-yl)-thiazol-5-yl]-piperazin-1-yl}-2-imidazo[4,5-b]pyridin-3-yl-ethanone;

2-(3,5-Dimethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-trifluoromethyl-[1,2,4]triazol-1-yl)-ethanone;

2-(3-Cyclobutyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(3-tert-Butyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(3-Cyclopropyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(3-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(5-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-isopropyl-[1,2,4]triazol-1-yl)-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(5-methyl-[1,2,4]triazol-1-yl)-ethanone;

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methoxymethyl-[1,2,4]triazol-1-yl)-ethanone; or 2-(3-Difluoromethyl-[1,2,4]triazol-1-yl)-1-{(R)-2-hydroxymethyl-4-[2-trifluoromethyl-4-(2-trifluoromethyl-pyrimidin-5-yl)-thiazol-5-yl]-piperazin-1-yl}-ethanone;

or a salt thereof.

12. The compound according to claim 1, wherein the compound is:

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

2-(3-Ethyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

2-(3-Cyclopropyl-pyrazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

1-{(S)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

2-(3-Ethyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone; or 2-(3-Cyclopropyl-pyrazol-1-yl)-1-{(S)-2-hydroxymethyl-4-[2-trifluoromethyl-4-(2-trifluoromethyl-pyrimidin-5-yl)-thiazol-5-yl]-piperazin-1-yl}-ethanone;

or a salt thereof.

13. A pharmaceutical composition comprising, as active principle, the compound according to claim 1, or a pharmaceutically acceptable salt thereof, and at least one therapeutically inert excipient.

14. The compound according to claim 1, or a pharmaceutically acceptable salt thereof, formulated as a medicament.

15. A method of treating a disease comprising administering to a subject in need thereof, an effective amount of the compound according to claim 1, wherein the disease is an autoimmune disorder, inflammatory disease, infectious disease, transplant rejection, fibrosis, neurodegenerative disorder, or cancer.

16. A method of treating a disease comprising administering to a subject in need thereof, an effective amount of the pharmaceutical composition according to claim 13, wherein the disease is an autoimmune disorder, inflammatory disease, infectious disease, transplant rejection, fibrosis, neurodegenerative disorder, or cancer.

17. The compound according to claim 1, wherein the compound is:

1-{(R)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

or a pharmaceutically acceptable salt thereof.

18. The compound according to claim 1, wherein the compound is:

2-(3-Cyclopropyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone;

or a pharmaceutically acceptable salt thereof.

19. The compound according to claim 1, wherein the compound is:

2-(3-Ethyl-[1,2,4]triazol-1-yl)-1-{(R)-2-(2-hydroxy-ethyl)-4-2-[trifluoromethyl-4-(2-trifluoromethyl-pyrimidin-5-yl)-thiazol-5-yl]-piperazin-1-yl}-ethanone;

or a pharmaceutically acceptable salt thereof.

20. The compound according to claim 1, wherein the compound is:

1-{(R)-2-(2-Hydroxy-ethyl)-4-[2-trifluoromethyl-4-(2-trifluoromethyl-pyrimidin-5-yl)-thiazol-5-yl]-piperazin-1-yl}-2-(3-methyl-[1,2,4]triazol-1-yl)-ethanone;

or a pharmaceutically acceptable salt thereof.

21. The compound according to claim 1, wherein the compound is:

1-{(S)-2-Hydroxymethyl-4-[2-trifluoromethyl-4-(2-trifluoromethyl-pyrimidin-5-yl)-thiazol-5-yl]-piperazin-1-yl}-2-(3-methyl-pyrazol-1-yl)-ethanone;

or a pharmaceutically acceptable salt thereof.

* * * * *

UNITED STATES PATENT AND TRADEMARK OFFICE
CERTIFICATE OF CORRECTION

Page 1 of 2

PATENT NO. : 10,053,457 B2
APPLICATION NO. : 15/543457
DATED : August 21, 2018
INVENTOR(S) : Eva Caroff et al.

It is certified that error appears in the above-identified patent and that said Letters Patent is hereby corrected as shown below:

In the Claims

Column 51, Claim 1, Line 39, replace "(C1-4)alkyl" with --$(C_{1-4})$alkyl--.

Column 51, Claim 2, Lines 53–54, replace "(C1-4)alkoxy" with --$(C_{1-4})$alkoxy--.

Column 52, Claim 5, Lines 5-23, replace the following Formula ($I_{TA}$):

"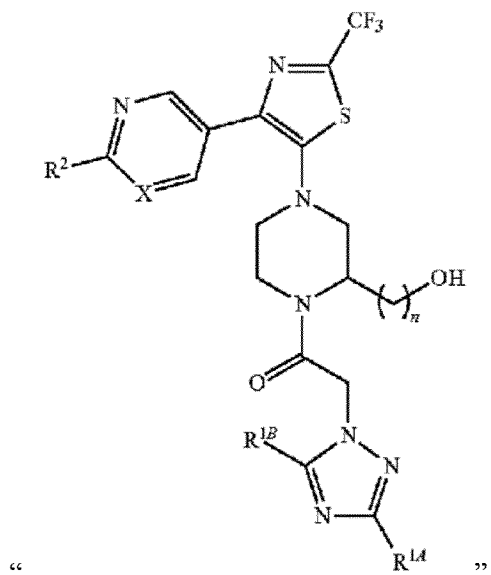"

Signed and Sealed this
Thirteenth Day of November, 2018

Andrei Iancu
*Director of the United States Patent and Trademark Office*

CERTIFICATE OF CORRECTION (continued)

With the following formula (I$_{TA}$):

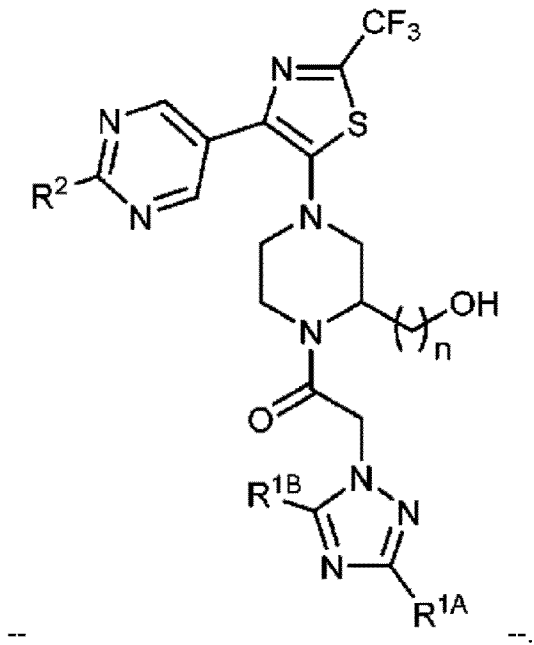

Column 56, Claim 19, Lines 13-15, replace the formula "2-(3-Ethyl-[1,2,4]triazol-1-yl)-1-{(R)-2-(2-hydroxy-ethyl)-4-2-[trifluoromethyl-4-(2-trifluoromethyl-pyrimidin-5-yl)-thiazol-5-yl]-piperazin-1-yl}-ethanone" with the formula --2-(3-Ethyl-[1,2,4]triazol-1-yl)-1-{(R)-2-(2-hydroxy-ethyl)-4-[2-trifluoromethyl-4-(2-trifluoromethyl-pyrimidin-5-yl)-thiazol-5-yl]-piperazin-1-yl}-ethanone--.